US010010616B2

(12) United States Patent
Borch et al.

(10) Patent No.: US 10,010,616 B2
(45) Date of Patent: Jul. 3, 2018

(54) IMMUNOGENIC COMPOSITIONS AND REAGENTS FOR PREPARING

(75) Inventors: Richard Frederic Borch, Lafayette, IN (US); Irene A. George, Lafayette, IN (US); Harm Hogenesch, West Lafayette, IN (US); Stanley L. Hem, West Lafayette, IN (US); Lawrence E. Hem, legal representative, West Lafayette, IN (US)

(73) Assignee: PURDUE RESEARCH FOUNDATION, West Lafayette, IN (US)

( * ) Notice: Subject to any disclaimer, the term of this patent is extended or adjusted under 35 U.S.C. 154(b) by 333 days.

(21) Appl. No.: 13/981,813

(22) PCT Filed: Jan. 27, 2012

(86) PCT No.: PCT/US2012/022919
§ 371 (c)(1),
(2), (4) Date: Aug. 6, 2014

(87) PCT Pub. No.: WO2012/103444
PCT Pub. Date: Aug. 2, 2012

(65) Prior Publication Data
US 2015/0023987 A1 Jan. 22, 2015

Related U.S. Application Data

(60) Provisional application No. 61/437,271, filed on Jan. 28, 2011.

(51) Int. Cl.
*A61K 39/385* (2006.01)
*A61K 39/39* (2006.01)
*A61K 47/48* (2006.01)
*A61K 38/45* (2006.01)
*A61K 38/47* (2006.01)
*A61K 39/395* (2006.01)
*C07K 16/28* (2006.01)
*C12N 9/96* (2006.01)
*A61K 39/00* (2006.01)

(52) U.S. Cl.
CPC ........ *A61K 47/48084* (2013.01); *A61K 38/45* (2013.01); *A61K 38/47* (2013.01); *A61K 39/39* (2013.01); *A61K 39/3955* (2013.01); *C07K 16/2896* (2013.01); *C12N 9/96* (2013.01); A61K 2039/505 (2013.01); A61K 2039/55505 (2013.01); A61K 2039/60 (2013.01); A61K 2039/627 (2013.01); C07K 2317/76 (2013.01); C12Y 204/02036 (2013.01); C12Y 302/01017 (2013.01)

(58) Field of Classification Search
CPC .............................. A61K 39/39; A61K 39/385
See application file for complete search history.

(56) References Cited

U.S. PATENT DOCUMENTS

| 4,828,982 A * | 5/1989 | Wagner ................ G01N 33/581 435/18 |
| 5,627,165 A | 5/1997 | Glazier |
| 5,730,985 A * | 3/1998 | Barber ............... A61K 39/0013 424/184.1 |
| 2005/0215562 A1 | 9/2005 | Tremblay et al. |
| 2007/0105092 A1* | 5/2007 | Paul ................... C07K 16/1063 435/5 |
| 2009/0304734 A1 | 12/2009 | Oscarson et al. |
| 2010/0061936 A1* | 3/2010 | Shen ..................... C07C 305/18 424/9.6 |

FOREIGN PATENT DOCUMENTS

WO    WO2006/037090    4/2006

OTHER PUBLICATIONS

Benjamin et al., "The Antigenic Structure of Bovine Serum Albumin", Journal of Biological Chemistry, vol. 253, No. 22, pp. 8087-8092, published Nov. 25, 1978.*
CAS RN 123300-08-3P (STN database entered Oct. 20, 1989) (Year: 1989).*
Anderer et al., "Cross-reactions of antisera against the terminal amino acid and dipeptide of tobacco mosaic verus", Biochimica et Biophysica Acta (BBA)—General Subjects, vol. 115, issue 1, pp. 222-224, published Jan. 25, 1966. (Year: 1966).*
PCT Search Report and Written Opinion for PCT/US2012/022919, completed May 3, 2012.
Flarend, Richard E., et al., "In Vivo Absorption of Aluminium-Containing Vaccine Adjuvants Using 26AL", 1997, Vaccine, vol. 15, No. 12/13, pp. 1314-1318.
Al-Shakhshir, Ragheb H., et al., "Contribution of Electrostatic and Hydrophobic Interactions to the Adsorption of Proteins by Aluminium-Containing Adjuvants", 1995, Vaccine, vol. 13, No. 1, pp. 41-44.
Arns, Steve, et al., "Design and Synthesis of Novel Bone-Targeting Dual-Action Pro-Drugs for the Treatment and Reversal of Osteoporosis", 2012, Bioorganic & Medicinal Chemistry, No. 20, pp. 2131-2140.
Shahani, Vijay M., et al., "Design, Synthesis and In Vitro Characterization of Novel Hybrid Peptidomimetic Inhibitors of STAT3 Protein", 2011, Bioorganic & Medicinal Chemistry, No. 19, pp. 1823-1838.
Hem, Stanley L., and Harm HogenEsch. "Relationship between physical and chemical properties of aluminum-containing adjuvants and immunopotentiation." Expert Review of Vaccines (2007): 685-698.

(Continued)

*Primary Examiner* — Tracy Vivlemore
*Assistant Examiner* — Nam P Nguyen
(74) *Attorney, Agent, or Firm* — Purdue Research Foundation; Zhigang Rao

(57) ABSTRACT

The invention described herein pertains to compounds and conjugates, to compositions, complexes and formulations comprising the compounds and/or conjugates, and to methods of use of the compounds, conjugates and their compositions, complexes and formulations in vaccines and vaccinations and generating immune responses.

10 Claims, 3 Drawing Sheets

(56) References Cited

OTHER PUBLICATIONS

Al-Shakhshir, Ragheb H., et al. "Contribution of electrostatic and hydrophobic interactions to the adsorption of proteins by aluminium-containing adjuvants." *Vaccine* 13.1 (1995): 41-44.

Boutselis, Irene G., et al. "Synthesis and cell-based activity of a potent and selective protein tyrosine phosphatase 1B inhibitor prodrug." *Journal of medicinal chemistry* 50.4 (2007): 856-864.

Xie, Laiping, et al. "Cellular effects of small molecule PTP1B inhibitors on insulin signaling." *Biochemistry* 42.44 (2003): 12792-12804.

Zhang, Yinsheng, et al. "A novel asymmetric synthesis of tritium and carbon-14 labeled (R)-ibuprofen." *Journal of Labelled Compounds and Radiopharmaceuticals* 49.3 (2006): 237-244.

Jeong, Sang Won, and David F. O'Brien. "Synthesis of a polymerizable metal-ion-chelating lipid for fluid bilayers." *The Journal of organic chemistry* 66.14 (2001): 4799-4802.

Taylor, Scott D., et al. "Synthesis of aryl(difluoromethylenephosphonates) via electrophilic fluorination of α-carbanions of benzylic phosphonates with N-fluorobenzenesulfonimide." *Tetrahedron* 54.9 (1998): 1691-1714.

* cited by examiner

IMMUNOGENIC COMPOSITIONS AND REAGENTS FOR PREPARING

CROSS-REFERENCE TO RELATED APPLICATIONS

This application is a national stage entry under 35 USC § 371(b) of International Application No. PCT/US2012/022919, filed Jan. 27, 2012, which claims the benefit under 35 USC § 119(e) of U.S. Provisional Application Ser. No. 61/437,271 filed on Jan. 28, 2011, the entire disclosures of which are incorporated herein by reference.

TECHNICAL FIELD

The invention described herein pertains to compounds and conjugates, to compositions, complexes and formulations comprising the compounds and/or conjugates, and to methods of use of the compounds, conjugates and their compositions, complexes and formulations in vaccines and vaccinations and/or for generating an immune response.

BACKGROUND AND SUMMARY OF THE INVENTION

Vaccination is a highly effective medical intervention aimed at reducing the morbidity and mortality caused by infectious diseases in animals, including humans. Vaccination induces an immune response against antigens present in the vaccine that protects against subsequent exposure to infectious agent(s). It has been reported that adsorption of an antigen to aluminum-containing adjuvants may in some cases enhance the immunogenicity of the antigen. It has also been reported that complexation of antigen with adjuvant may in other cases facilitate uptake of antigen in the antigen-presenting dendritic cells (Hem and HogenEsch, *Expert Review of Vaccines* 2007, 6, 685-698; the preceding publication, and all other publications cited herein, are incorporated herein by reference in their entirety). Thus, adjuvants are substances often added to vaccines to achieve a more effective immune response (*Rev. Inf. Dis.* 1980, 2, 370; *Nat. Rev. Microbiol.* 2007, 5, 505).

In particular, aluminum adjuvants are often added. It is appreciated that currently, only aluminum adjuvants have been approved for use in human vaccines by the Food and Drug Administration. Aluminum adjuvants have a long (>60 years) record of safety. The adjuvant aluminum hydroxide (AH) consists of small primary particles less than 50 nm in size that form loose aggregates about 1-20 μm in diameter (*Expert Rev. Vaccines* 2007, 5, 685). The particulate nature gives the aluminum adjuvant a very large adsorptive capacity. The two main mechanisms of adsorption are electrostatic adsorption and ligand exchange adsorption. The surface of AH contains only hydroxyl groups that give it a positive surface charge at neutral pH, and a high capacity for ligand exchange. Ligand exchange involves the substitution of —OH groups at the surface by phosphate groups present on the antigen, resulting in strong binding of the molecule to which the phosphate group is attached.

For protein antigens that naturally contain phosphorylated amino acids (typically phosphoserine or phosphothreonine) such complexation may be straightforward. In cases where the proteins do not contain phosphate groups, or sufficient phosphate groups, such groups must be introduced in a separate step prior to combining the protein and aluminum hydroxide adjuvant. It has been reported that phosphate groups may be introduced by combining the protein, phosphoserine, and a peptide coupling reagent, such as a carbodiimide, to form a covalent amide bond between the added phosphoserine carboxyl group and amine groups (typically lysine) on the protein. However, it is observed that such a process will also form amide bonds between amino and carboxyl groups on the protein molecules themselves, thus forming protein oligomers, such as dimers, trimers, etc., forming crosslinks within the protein, and generally leading to a complicated mixture of components in the prepared formulation. New reagents and processes are needed for preparing such protein formulations.

In one illustrative embodiment of the invention herein, reagents for preparing immunogenic compositions are described herein. In another embodiment, reagents for attaching one or more phosphates or phosphate mimetic groups to a protein or peptide are described.

In another embodiment, described herein are methods for attaching a protein or peptide to an adjuvant. In another embodiment, described herein are methods for preparing a peptide or protein immunogenic compound or vaccine, where the peptide or protein immunogenic compound or vaccine comprises a complex of the protein or peptide with an adjuvant. In another illustrative embodiment, the adjuvant is an aluminum hydroxide.

In another embodiment, described herein are conjugate molecules composed of three moieties: A phosphate or phosphomimetic group at one end, a spacer or linker, and an active (N-hydroxysuccinimide) ester at the other end. In one illustrative aspect, the active ester is capable of coupling with reactive groups on the protein or peptide, such as on the surface of a protein or peptide (illustratively amino groups, such as but not limited to those on lysine residues in the protein or peptide, and/or hydroxyl or thiol groups, such as but not limited to those on serine, threonine, and cysteine residues in the protein or peptide). Successful coupling of these molecules with a protein or peptide provides one or more phosphate or phosphomimetic groups on the surface of the protein or peptide. Without being bound by theory, it is believed that the "phosphorylation" of the protein or peptide increases the affinity for adjuvants, such as aluminum hydroxide adjuvants, and enhances the utility of the protein or peptide as an immunogenic compound or vaccine. It has been reported that existing strategies to introduce phosphate groups into proteins lead to undesired modifications of the protein, as described herein. The molecules of the invention described herein introduce phosphate or phosphomimetic groups without undesired modification of the protein or peptide.

In another embodiment, conjugates are described herein for increasing the binding of antigens to adjuvants.

In another embodiment, conjugates are described herein for increase the immunogenicity of antigens.

In another embodiment, conjugates and processes for preparing conjugates are described herein for modifying the affinity of antigens for adjuvants. In one aspect, the affinity may be tuned between low, moderate, and high affinity as needed for various configurations of the conjugates, immunogenic compositions, and/or vaccines described herein. Without being bound by theory, it is believed herein that the degree of conjugation or loading is related to the affinity for adjuvants, where a higher affinity is observed when there is higher conjugation loading.

In another illustrative embodiment, described herein is a compound of the formula

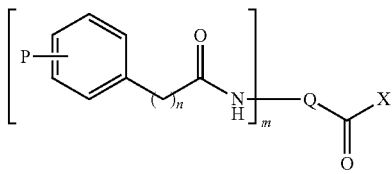

wherein
P is a phosphorus containing group;
X is a leaving group;
Q is polyvalent linker;
m is an integer in the range from 1 to about 3; and
n is an integer in the range from 1 to about 20.

In another illustrative embodiment of the compounds described herein, Q is polyvalent heteroalkylene. In another illustrative embodiment, Q is alkyleneamino(alkyl)$_2$, where each alkyl is independently selected. In another illustrative embodiment, m is 2.

In another illustrative embodiment, described herein is a compound of the formula

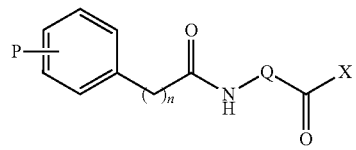

wherein P is a phosphorus containing group; X is a leaving group; Q is a polyvalent linker, including but not limited to alkylene, heteroalkylene, or poly(oxyalkylene) each of which is optionally substituted; and n is an integer in the range from 1 to about 20.

DETAILED DESCRIPTION

Figure 1:
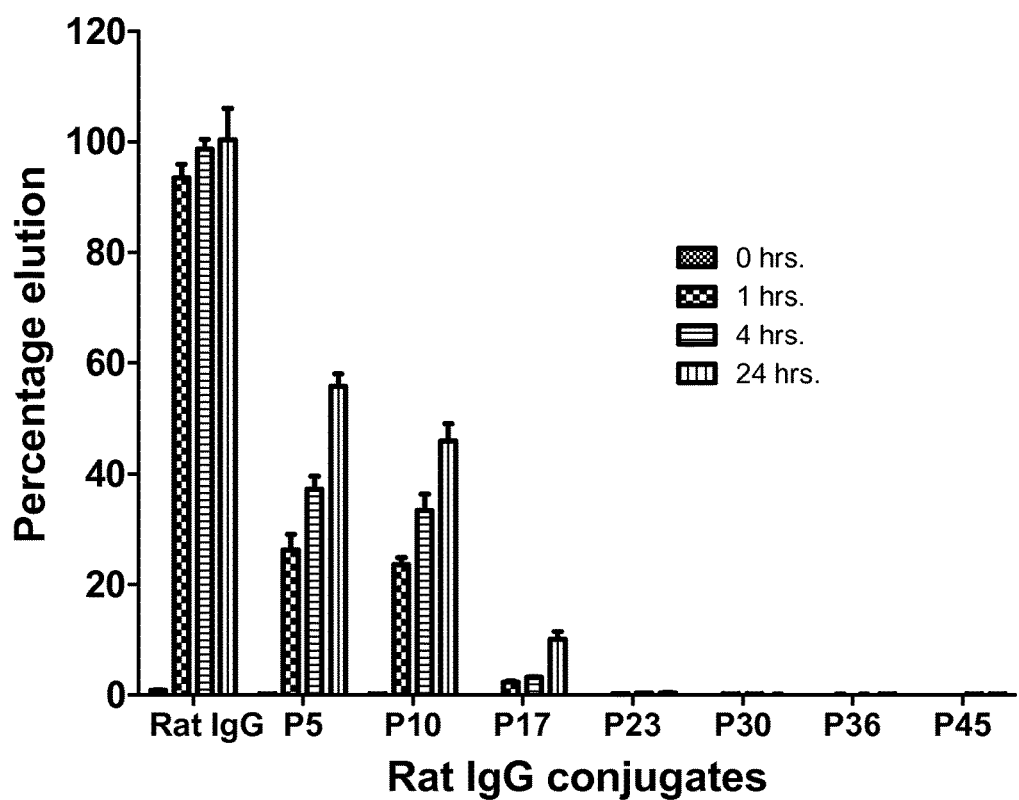
FIG. 1 shows time-dependent elution of protein for compound B-Rat IgG conjugates containing 5-17 linkers.

Described herein are linkers capable of attaching proteins and/or peptides to adjuvants. In one aspect, the proteins or peptides are antigens and the adjuvants are immunogenic or vaccine adjuvants. In one illustrative embodiment, the adjuvant is an aluminum hydroxide adjuvant. In another embodiment, described herein are methods for preparation of the linkers herein. In another embodiment, described herein are methods for the use of the linkers for the preparation of conjugates comprising proteins attached to adjuvants via the linkers. In another embodiment, described herein are methods for use of the conjugates, as well as compositions, complexes and formulations comprising the conjugates, in immunogenic therapies, such as in vaccines and vaccination.

It is appreciated that the reagents described herein may decrease the formation of unwanted side products, such as protein or peptide oligomers, compared to conventional processes that use a generic coupling reagent. In one aspect, the reagents described herein contain an active ester of a carboxylic acid, which may react more selectively with nucleophilic functional groups on the protein or peptide. In another embodiment, a specific "reagent+protein/peptide=phosphorylated protein/peptide" reaction occurs without other modifications of the protein or peptide taking place.

In another embodiment, described herein is a compound of the formula

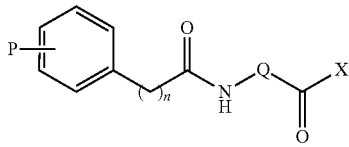

wherein P is a phosphorus containing group; X is a leaving group; Q is a polyvalent linker, such as alkylene or heteroalkylene, each of which is optionally substituted; and n is an integer in the range from 1 to about 20.

In another embodiment, described herein is the compound as described above, wherein Q is poly(oxyalkylene).

In another embodiment, described herein is the compound as described above, wherein Q is alkylene. In one illustrative aspect, Q is C1 to C20 alkylene. In another illustrative aspect, Q is C4 to C8 alkylene. In another illustrative aspect, Q is C4 to C6 alkylene. In yet another illustrative aspect, Q is C5 alkylene.

In another embodiment, described herein is the compound as described above, wherein n is 1 or 2. In one aspect, n is 1.

In another embodiment, described herein is the compound as described above, wherein X is N-hydroxysuccinimide.

In another embodiment, described herein is the compound as described above, wherein P is a radical of the formula (RO)$_2$PZ; where R is independently selected in each instance from the group consisting of hydrogen, alkyl, aryl, arylalkyl, heteroaryl, heteroarylalkyl, oxygen protecting groups, and oxygen prodrug groups; and X is oxygen, or nitrogen or alkylene, each of which is optionally substituted; and wherein Z is independently selected in each instance from the group consisting of NH, oxygen, methylene, a fluorinated alkylene, and difluoromethylene.

In another embodiment, described herein is the compound as described above, wherein Z is NH.

In another embodiment, described herein is the compound as described above, wherein Z is oxygen.

In another embodiment, described herein is the compound as described above, wherein Z is methylene.

In another embodiment, described herein is the compound as described above, wherein Z is a fluorinated alkylene.

In another embodiment, described herein is the compound as described above, wherein Z is difluoromethylene.

In another embodiment, described herein is a conjugate comprising a protein or peptide covalently attached to one or more phosphates or derivatives thereof, one or more phosphomimetics or derivatives thereof, or a combination thereof, each through an independently selected linker.

In another embodiment, described herein is the conjugate as described above wherein the phosphomimetic or derivative thereof is a radical of the formula (RO)$_2$PX; where R is independently selected in each instance from the group consisting of hydrogen, alkyl, aryl, arylalkyl, heteroaryl, heteroarylalkyl, oxygen protecting groups, and oxygen prodrug groups; and X is oxygen, or nitrogen or alkylene, each of which is optionally substituted.

In another embodiment, described herein is the conjugate as described above where the protein or peptide includes a lysine, and wherein the lysine is covalently attached to the phosphate or derivative thereof, or the phosphomimetic or derivative thereof, each through an independently selected linker.

In another embodiment, described herein is the conjugate as described above wherein the phosphomimetic is a phosphonate. In another embodiment, the phosphomimetic is a difluoromethylene phosphonate.

In another embodiment, described herein is the conjugate as described above wherein the protein or peptide is an antigen. In another embodiment, the protein or peptide is capable of functioning as an immunogenic compound and/or vaccine.

In another embodiment, polyvalent linker Q is a chain of atoms selected from C, N, O, S, Si, and P, and combinations thereof. The linker may have a wide variety of lengths, such as in the range from about 2 to about 100 atoms. The atoms used in forming the linker may be combined in all chemically relevant ways, such as chains of carbon atoms forming alkylene, alkenylene, and alkynylene groups, and the like; chains of carbon and oxygen atoms forming ethers, polyoxyalkylene groups, or when combined with carbonyl groups forming esters and carbonates, and the like; chains of carbon and nitrogen atoms forming amines, imines, polyamines, hydrazines, hydrazones, or when combined with carbonyl groups forming amides, ureas, semicarbazides, carbazides, and the like; chains of carbon, nitrogen, and oxygen atoms forming alkoxyamines, alkoxylamines, or when combined with carbonyl groups forming urethanes, amino acids, acyloxylamines, hydroxamic acids, and the like; and many others. In addition, it is to be understood that the atoms forming the chain in each of the foregoing illustrative embodiments may be either saturated or unsaturated, such that for example, alkanes, alkenes, alkynes, imines, and the like may be radicals that are included in the linker. In addition, it is to be understood that the atoms forming the linker may also be cyclized upon each other to form divalent cyclic structures that form the linker, including cyclo alkanes, cyclic ethers, cyclic amines, arylenes, heteroarylenes, and the like in the linker. It is to be further understood that the atoms forming the linker are optionally substituted, such as described herein.

In another embodiment, described herein is the conjugate as described above wherein the linker is an optionally substituted aryl group. In one embodiment, the aryl group is a radical of the formula

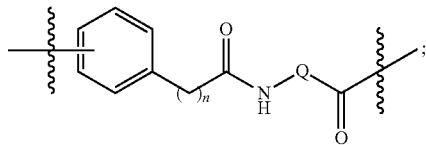

P is a phosphorus containing group; X is a leaving group; Q is alkylene or heteroalkylene, each of which is optionally substituted; and n is an integer in the range from 1 to about 20.

In another embodiment, described herein are the compounds or conjugates as described above, wherein Q is poly(oxyalkylene). In another embodiment, Q is alkylene. In one aspect, Q is C1 to C20 alkylene. In another aspect, Q is C4 to C8 alkylene. In another aspect, Q is C4 to C6 alkylene. In yet another aspect, Q is C5 alkylene.

In another embodiment, described herein are the compounds or conjugates as described above, wherein n is 1 or 2. In another embodiment, n is 1.

In another embodiment, described herein are the compounds or conjugates as described above, wherein P is a radical of the formula $(RO)_2PZ$; where R is independently selected in each instance from the group consisting of hydrogen, alkyl, aryl, arylalkyl, heteroaryl, heteroarylalkyl, oxygen protecting groups, and oxygen prodrug groups; and X is oxygen, or nitrogen or alkylene, each of which is optionally substituted. In another embodiment, Z is NH. In another embodiment, Z is oxygen. In another aspect, Z is methylene. In another embodiment, Z is a fluorinated alkylene. In another embodiment, Z is difluoromethylene.

In another embodiment, described herein are the compounds or conjugates as described above, wherein Q is about C4 to about C10 alkylene. In another embodiment, Q is about C4 to about C6 alkylene. In another embodiment, Q is C5 alkylene In another embodiment, described herein is a composition comprising any of the compounds or conjugates described above, further comprising one or more carriers, diluents, or excipients, or a combination thereof.

In another embodiment, described herein is a complex comprising one or more of the conjugates described above, and an adjuvant.

In another embodiment, described herein is a complex comprising two or more of the conjugates described above, and an adjuvant.

In another embodiment, described herein are the conjugates or complexes as described above wherein the protein or peptide is an antigen.

In another embodiment, described herein are the conjugates or complexes as described above configured to function as an immunogenic compound and/or vaccine.

In another embodiment, described herein are the conjugates or complexes as described above wherein the adjuvant is aluminum hydroxide.

In another embodiment, described herein is the complex as described above wherein the complex is characterized by at least about 50%, at least about 60%, or at least about 70% stability in interstitial fluid for a predetermined period of time, such as over 24 hours. In one illustrative aspect, stability in interstitial fluid is characterized by the ability of the complex to remain attached to the adjuvant, such as an aluminum hydroxide adjuvant.

In another embodiment, described herein is a pharmaceutical composition comprising the conjugate as described above, the complex as described above, or a combination thereof.

In another embodiment, described herein is the pharmaceutical composition described above, further comprising one or more carriers, diluents, or excipients, or a combination thereof.

In another embodiment, described herein is a unit dose or a unit dosage form comprising a therapeutically effective amount of the pharmaceutical composition as described above for vaccination.

In another embodiment, described herein is a method for vaccinating a patient, the method comprising the step of administering to the patient a therapeutically effective amount of one or more the conjugates, complexes, or compositions described above, or a combination thereof.

In another embodiment, described herein is a kit for preparing a protein and/or peptide composition, the kit comprising a predetermined amount of one or more of the compounds described above, a predetermined amount of one or more adjuvants, and instructions for use, where the kit is adapted for use with a protein and/or peptide, or a combination thereof.

In another embodiment, described herein is a kit as described above wherein the protein or peptide is an antigen.

In another embodiment, described herein is a kit as described above wherein the conjugate or formulation is configured to function as an immunogenic compound and/or vaccine.

In another embodiment, described herein is a kit as described above wherein the adjuvant is aluminum hydroxide.

It is to be understood that the compounds or conjugates described herein may contain one or more chiral centers, or may otherwise be capable of existing as multiple stereoisomers. It is to be understood that in one embodiment, the invention described herein is not limited to any particular sterochemical requirement, and that the compounds, conjugates and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain is cyclic. It is to be understood that cycloalkylalkyl is a subset of cycloalkyl. It is also to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, heteroarylamino, heteroarylalkylamino, heteroarylalkenylamino, heteroarylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, heteroaryloxy, heteroarylalkyloxy, heteroarylalkenyloxy, heteroarylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, heteroarylthio, heteroarylalkylthio, heteroarylalkenylthio, heteroarylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, heteroarylcarbonyl, heteroarylalkylcarbonyl, heteroarylalkenylcarbonyl, heteroarylalkynylcarbonyl, acylcarbonyl, and the like, each of which is optionally substituted.

As used herein, the term "carbonyl and derivatives thereof" includes the group C(O), C(S), C(NH) and substituted amino derivatives thereof.

As used herein, the term "carboxylate and derivatives thereof" includes the group $CO_2H$ and salts thereof, and esters and amides thereof, and CN.

As used herein, the term "sulfonyl or a derivative thereof" includes $SO_3H$ and salts thereof, and esters and amides thereof.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

As used herein, the terms "optionally substituted aryl" and "optionally substituted heteroaryl" include the replacement of hydrogen atoms with other functional groups on the aryl or heteroaryl that is optionally substituted. Such other functional groups illustratively include, but are not limited to, amino, hydroxy, halo, thio, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof, and the like. Illustratively, any of amino, hydroxy, thio, alkyl, haloalkyl, heteroalkyl, aryl, arylalkyl, arylheteroalkyl, heteroaryl, heteroarylalkyl, heteroarylheteroalkyl, and/or sulfonic acid is optionally substituted.

Illustrative substituents include, but are not limited to, a radical $—(CH_2)_xZ^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from $—CO_2R^4$ and $—CONR^5R^6$, where $R^4$, $R^5$, and $R^6$ are each independently selected in each occurrence from hydrogen, $C_1$-$C_6$ alkyl, aryl-$C_1$-$C_6$ alkyl, and heteroaryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —$CO_2H$, —$NR_2$. Illustrative prodrugs include but are not limited to carboxylate esters where the group is alkyl, aryl, arylalkyl, heteroaryl, heteroarylalkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, ($C_3$-$C_{20}$)alkanoyl; halo-($C_3$-$C_{20}$)alkanoyl; ($C_3$-$C_{20}$)alkenoyl; ($C_4$-$C_7$)cycloalkanoyl; ($C_3$-$C_6$)-cycloalkyl($C_2$-$C_{16}$)alkanoyl; optionally substituted aroyl, such as unsubstituted aroyl or aroyl substituted by 1 to 3 substituents selected from the group consisting of halogen, cyano, trifluoromethanesulphonyloxy, ($C_1$-$C_3$)alkyl and ($C_1$-$C_3$)alkoxy, each of which is optionally further substituted with one or more of 1 to 3 halogen atoms; optionally substituted aryl($C_2$-$C_{16}$)alkanoyl and optionally substituted heteroaryl($C_2$-$C_{16}$)alkanoyl, such as the aryl or heteroaryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulfonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill.

It is also appreciated that the therapeutically effective amount, whether referring to monotherapy or combination therapy, is advantageously selected with reference to any toxicity, or other undesirable side effect, that might occur during administration of one or more of the compounds described herein. Further, it is appreciated that the co-therapies described herein may allow for the administration of lower doses of compounds that show such toxicity, or other undesirable side effect, where those lower doses are below thresholds of toxicity or lower in the therapeutic window than would otherwise be administered in the absence of a cotherapy.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, ($21^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

It is appreciated that compounds described herein can exist in unsolvated forms as well as solvated forms, including hydrated forms. It is to be understood that the solvated forms and the unsolvated forms are described herein, either individually or collectively with reference to the compounds and compositions. It is also to be understood that the compounds described herein may exist in multiple amorphous, non-amorphous, partially crystalline, crystalline, and/or other morphological forms. In general, all physical forms are described for the uses contemplated herein and are intended to be included in the methods, uses, compositions, and medicaments described herein. It is also to be understood that the compounds described herein may be present in the form of a salt.

In another embodiment, the invention described herein is illustrated by the following numbered clauses:

1. A conjugate comprising a protein or peptide covalently attached to one or more phosphorus containing groups P, each through an independently selected linker, where each P is an independently selected phosphate or derivatives thereof, or phosphomimetic or derivative thereof.

2. The conjugate as described in the preceding clause where the protein or peptide includes one or more lysines, and wherein at least one lysine is covalently attached to P through an independently selected linker.

3. The conjugate as described in any one of the preceding clauses wherein the protein is an antigen.

4. The conjugate as described in any one of the preceding clauses wherein the peptide is an antigen.

5. The conjugate as described in any one of the preceding clauses wherein the conjugate is configured to function as an immunogenic compound and/or vaccine.

6. The conjugate as described in any one of the preceding clauses wherein the linker is an optionally substituted aryl group.

7. The conjugate as described in any one of the preceding clauses wherein the aryl group is a radical of the formula

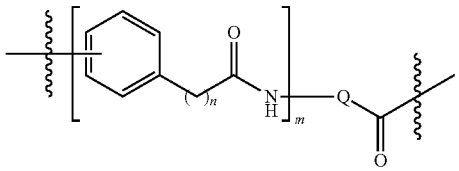

wherein
Q is polyvalent linker;
m is an integer in the range from 1 to about 3; and
n is an integer in the range from 1 to about 20.

8. The conjugate as described in any one of the preceding clauses wherein the aryl group is a radical of the formula

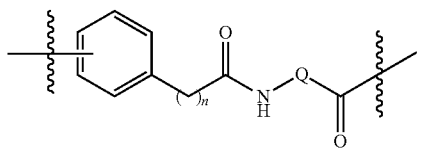

wherein
Q is alkylene or heteroalkylene, each of which is optionally substituted; and
n is an integer in the range from 1 to about 20.

9. A compound of the formula

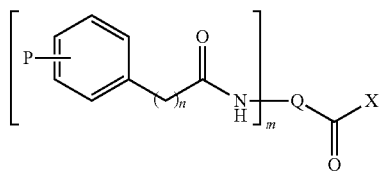

wherein
P is a phosphorus containing group;
X is a leaving group;
Q is polyvalent linker;
m is an integer in the range from 1 to about 3; and
n is an integer in the range from 1 to about 20.

10. The conjugate or compound as described in any one of the preceding clauses wherein m is 2.

11. The conjugate or compound as described in any one of the preceding clauses wherein m is 1.

12. A compound of the formula

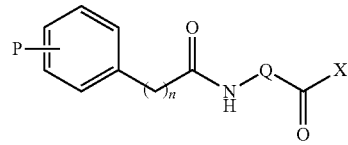

wherein
P is a phosphorus containing group;
X is a leaving group;
Q is alkylene or heteroalkylene, each of which is optionally substituted; and
n is an integer in the range from 1 to about 20.

13. The conjugate or compound as described in the preceding clause wherein Q is polyvalent optionally substituted heteroalkylene.

14. The conjugate or compound as described in the preceding clause wherein Q is polyvalent heteroalkylene.

15. The conjugate or compound as described in any one of the preceding clauses wherein Q is optionally substituted alkyleneamino(alkyl)$_2$, where each alkyl is independently selected.

16. The conjugate or compound as described in any one of the preceding clauses wherein Q is alkyleneamino(alkyl)$_2$, where each alkyl is independently selected.

17. The conjugate or compound as described in any one of the preceding clauses wherein Q is optionally substituted poly(oxyalklene).

18. The conjugate or compound as described in any one of the preceding clauses wherein Q is poly(oxyalklene).

19. The conjugate or compound as described in any one of the preceding clauses wherein Q is optionally substituted alkylene.

20. The conjugate or compound as described in any one of the preceding clauses wherein Q is alkylene.

21. The conjugate or compound as described in any one of the preceding clauses wherein Q is optionally substituted C1 to C20 alkylene.

22. The conjugate or compound as described in any one of the preceding clauses wherein Q is C1 to C20 alkylene.

23. The conjugate or compound as described in any one of the preceding clauses wherein Q is optionally substituted C4 to C8 alkylene.

24. The conjugate or compound as described in any one of the preceding clauses wherein Q is C4 to C8 alkylene.

25. The conjugate or compound as described in any one of the preceding clauses wherein Q is optionally substituted C4 to C6 alkylene.

26. The conjugate or compound as described in any one of the preceding clauses wherein Q is C4 to C6 alkylene.

27. The conjugate or compound as described in any one of the preceding clauses wherein Q is optionally substituted C5 alkylene.

28. The conjugate or compound as described in any one of the preceding clauses wherein Q is C5 alkylene.

29. The conjugate or compound as described in any one of the preceding clauses wherein n is 1 or 2.

30. The conjugate or compound as described in any one of the preceding clauses wherein n is 1.

30. The compound as described in any one of the preceding clauses wherein X is N-hydroxysuccinimide.

32. The conjugate or compound as described in any one of the preceding clauses wherein P is a phosphate.

33. The conjugate or compound as described in any one of the preceding clauses wherein P is a phosphonate.

34. The conjugate or compound as described in any one of the preceding clauses wherein P is a difluoromethylene phosphonate.

35. The conjugate or compound as described in any one of the preceding clauses wherein P is a radical of the formula

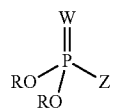

where R is independently selected in each instance from the group consisting of hydrogen and pharmaceutically acceptable cations, and alkyl, aryl, arylalkyl, heteroaryl, and heteroarylalkyl, each of which is optionally substituted, and oxygen protecting groups, and oxygen prodrug groups; W is oxygen or sulfur; and Z is oxygen or sulfur, or Z is nitrogen or alkylene, each of which is optionally substituted.

36. The conjugate or compound as described in any one of the preceding clauses wherein P is a radical of the formula

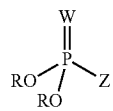

where R is independently selected in each instance from the group consisting of hydrogen, alkyl, aryl, arylalkyl, heteroaryl, heteroarylalkyl, oxygen protecting groups, and oxygen prodrug groups; W is oxygen; and Z is oxygen, or Z is nitrogen or alkylene, each of which is optionally substituted.

37. The conjugate or compound as described in any one of the preceding clauses wherein W is oxygen.

38. The conjugate or compound as described in any one of the preceding clauses wherein Z is optionally substituted NH.

39. The conjugate or compound as described in any one of the preceding clauses wherein Z is NH.

40. The conjugate or compound as described in any one of the preceding clauses wherein Z is oxygen.

41. The conjugate or compound as described in any one of the preceding clauses wherein Z is methylene.

42. The conjugate or compound as described in any one of the preceding clauses wherein Z is a fluorinated alkylene.

43. The conjugate or compound as described in any one of the preceding clauses wherein Z is difluoromethylene 44. The compounds or conjugates as described in any one of the preceding clauses wherein Q is about C4 to about C10 alkylene.

45. The compounds or conjugates as described in any one of the preceding clauses wherein n is 1 or 2.

46. The compounds or conjugates as described in any one of the preceding clauses wherein n is 1.

47. The compounds or conjugates as described in any one of the preceding clauses wherein Q is about C4 to about C6 alkylene.

48. The compounds or conjugates as described in any one of the preceding clauses wherein Q is C5 alkylene.

49. A composition comprising any of the compounds or conjugates of any one of the preceding clauses, further comprising one or more carriers, diluents, or excipients, or a combination thereof.

50. A complex comprising one or more conjugates of any one of the preceding clauses, and an adjuvant.

51. The complex as described in any one of the preceding clauses wherein at least one conjugate is of a protein or peptide.

52. The conjugates or complexes as described in any one of the preceding clauses wherein the protein or peptide is an antigen.

53. The conjugates or complexes as described in any one of the preceding clauses wherein the conjugates or complexes are configured to function as an immunogenic compound and/or vaccine.

54. The conjugates or complexes as described in any one of the preceding clauses wherein the adjuvant is aluminum hydroxide.

55. The complex as described in any one of the preceding clauses wherein the complex is characterized by at least about 50%, at least about 60%, or at least about 70% stability in interstitial fluid.

56. The complex as described in the preceding clause wherein stability in interstitial fluid is characterized by the ability of the complex to remain attached to the adjuvant.

57. The complex as described in any one of the preceding clauses wherein the adjuvant is an aluminum hydroxide adjuvant.

58. A pharmaceutical composition comprising the conjugate of any one of the preceding clauses, the complex of any one of the preceding clauses, or a combination thereof.

59. The composition of any one of the preceding clauses further comprising one or more carriers, diluents, or excipients, or a combination thereof.

60. A unit dose or a unit dosage form comprising a therapeutically effective amount of the pharmaceutical composition of any one of the preceding clauses for vaccination.

61. A kit for preparing a protein or peptide composition, the kit comprising a predetermined amount of one or more compounds of any one of clauses 1 to 20 or 38 to 56, a predetermined amount of one or more adjuvants, and instructions for use, where the kit is adapted for use with a protein or peptide, or a combination thereof.

62. The kit as described in the preceding clause wherein the protein or peptide is an antigen.

63. The kit as described in any one of the preceding clauses wherein the protein or peptide composition is configured to function as an immunogenic compound and/or vaccine.

64. The kit as described in any one of the preceding clauses wherein the adjuvant is aluminum hydroxide.

65. A method for vaccinating a patient, the method comprising the step of administering to the patient a therapeutically effective amount of one or more conjugates, complexes, or compositions, of any one of the preceding clauses, or a combination thereof.

In another embodiment, compounds of the following formulae are described
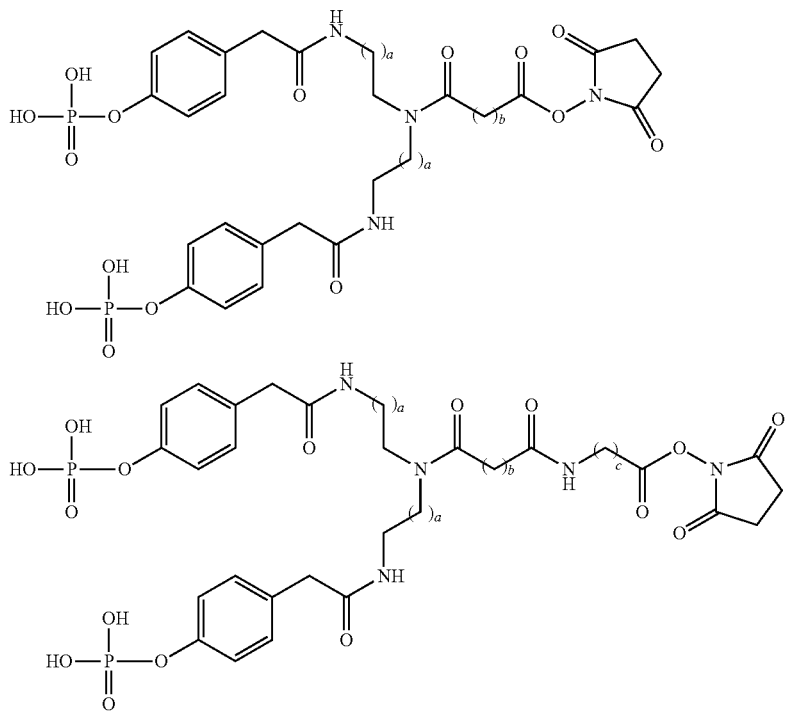
where a is an integer from 1 to about 3, or from 1 to about 2; b is an integer from 0 to about 9, or from 1 to about 6, or from 1 to about 5, or from 3 to about 5; and c is an integer from 1 to about 9, or form 1 to about 6, or from 1 to about 5, or from 3 to about 5.
In another embodiment, compounds of the following formulae are described
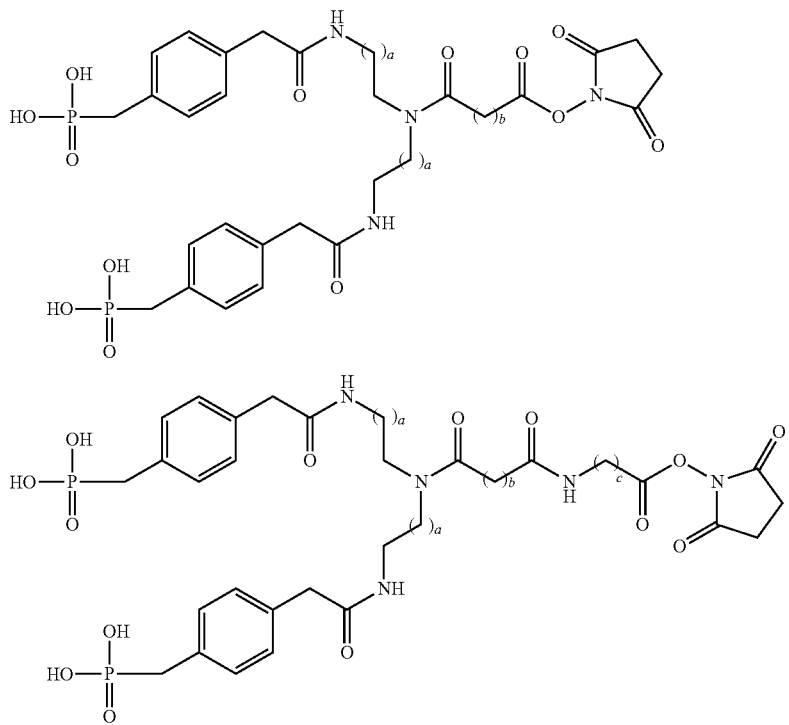

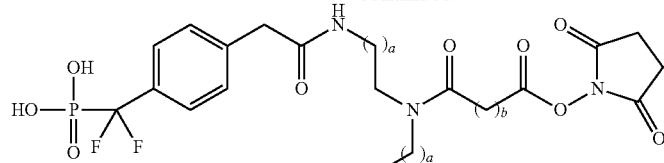
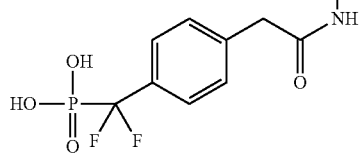
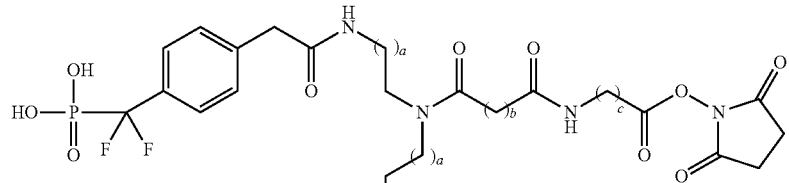
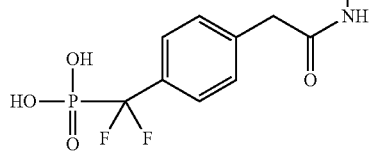
30
where a is an integer from 1 to about 3, or from 1 to about 2; b is an integer from 0 to about 9, or from 1 to about 6, or from 1 to about 5, or from 3 to about 5; and c is an integer from 1 to about 9, or form 1 to about 6, or from 1 to about 5, or from 3 to about 5.
In another embodiment, compounds of the following formulae are described
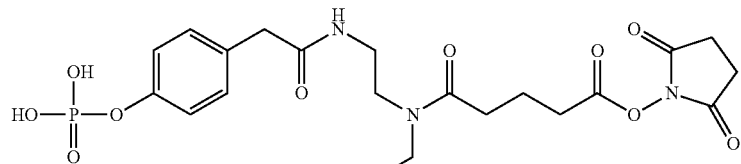
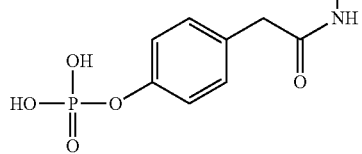
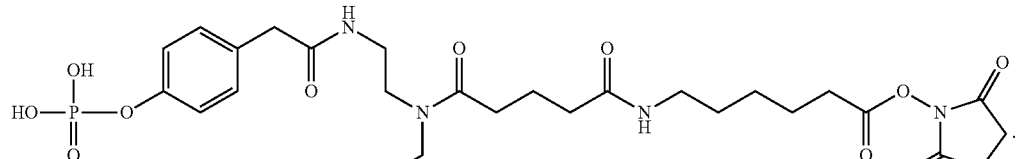
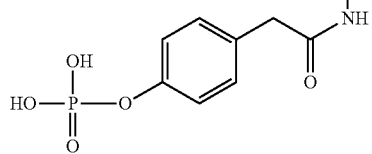

In another embodiment, compounds of the following formulae are described
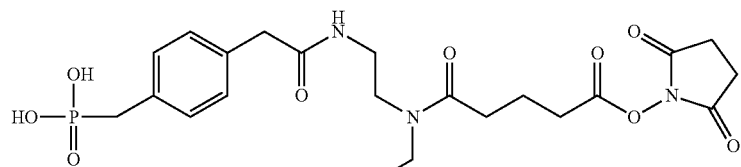
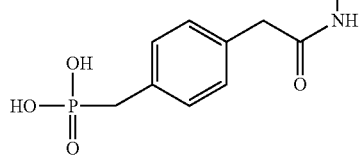
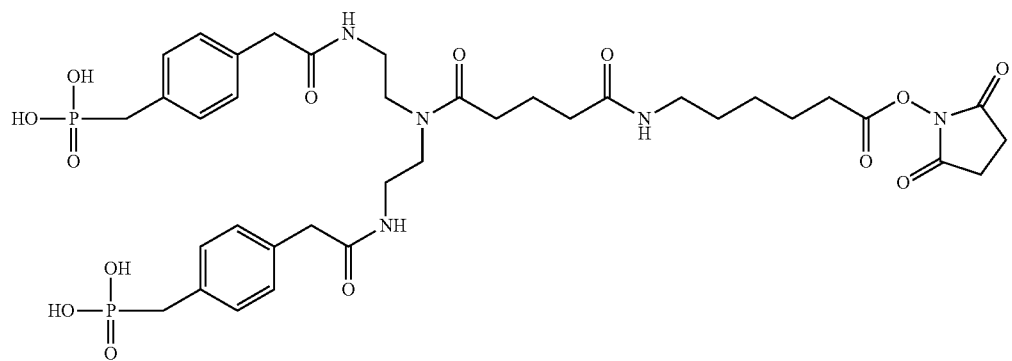
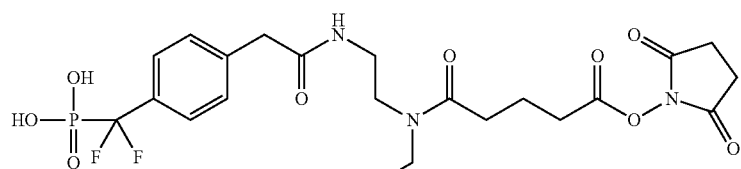
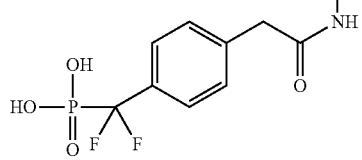
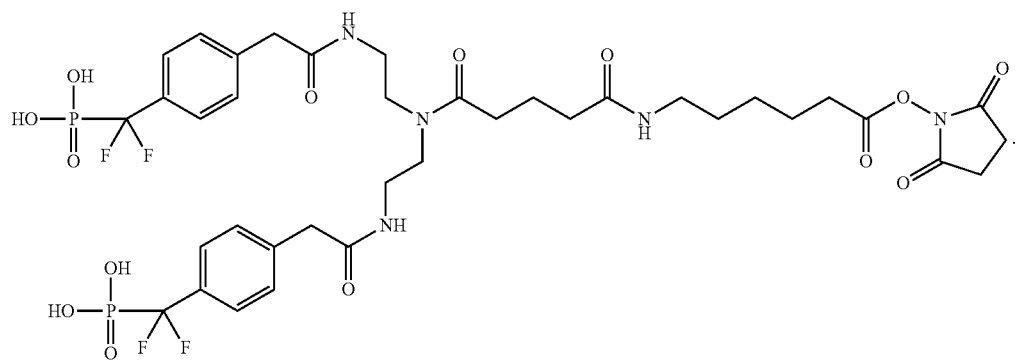

In another embodiment, compounds of the following formulae are described
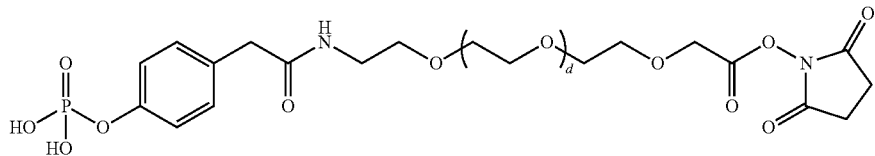
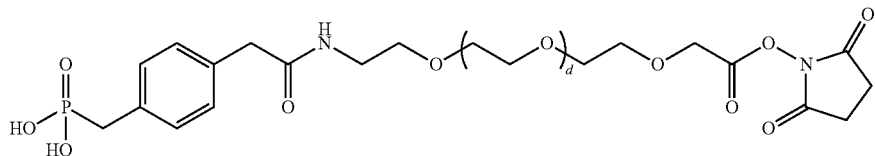
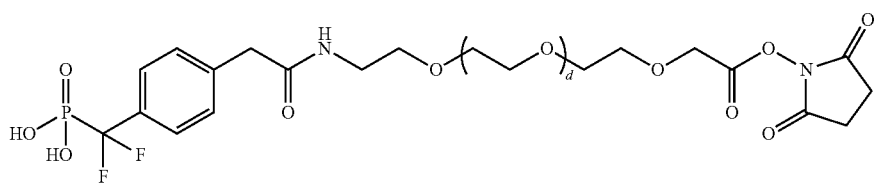
where d is an integer from 0 to about 50, or from 0 to about 10, or form 0 to about 5, or from 1 to about 5, or from 1 to about 3.
In another embodiment, compounds of the following formulae are described
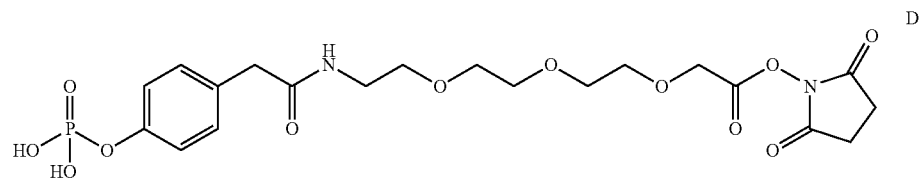
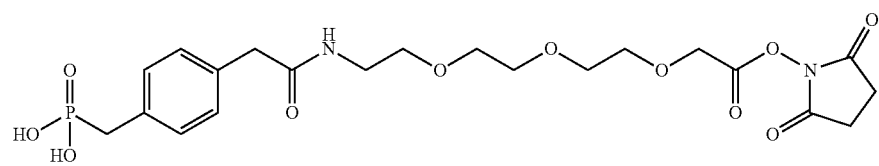
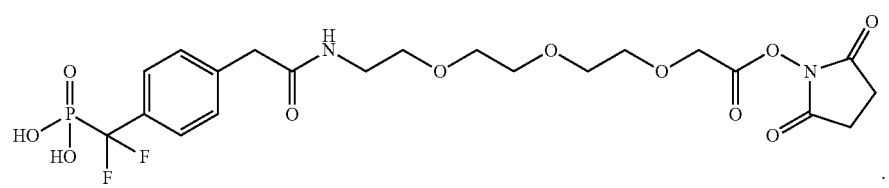

In another embodiment, compounds of the following formulae are described

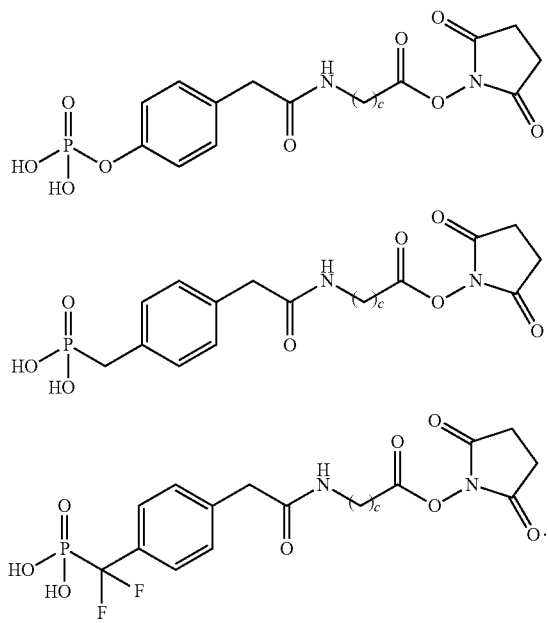

In another embodiment, compounds of the following formulae are described

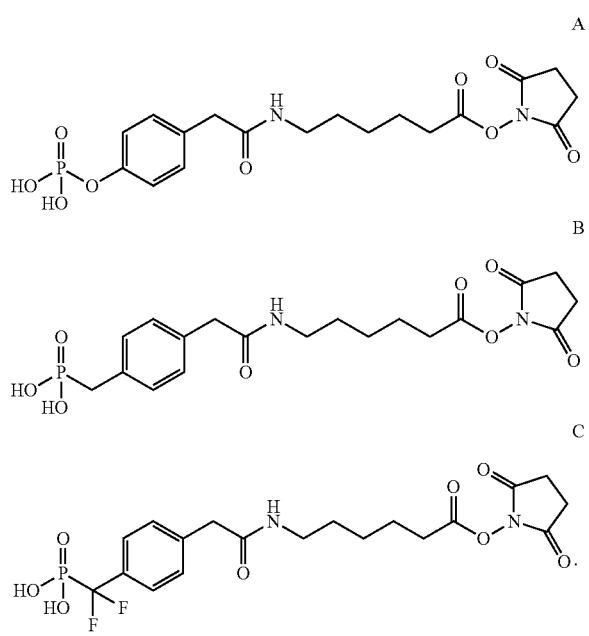

A

B

C

The following examples further illustrate additional features of the various embodiments of the invention described herein. However, it is to be understood that the examples are illustrative and are not to be construed as limiting other embodiments of the invention described herein. In addition, it is appreciated that other variations of the examples are included in the various embodiments of the invention described herein.

METHODS AND EXAMPLES

Method Example

The phosphorus containing groups described herein bind adjuvants. Compounds containing a phosphorus containing group and a UV chromophore are prepared and quantitative binding data are obtained as adsorption isotherms. Briefly, Rehydragel HPA aluminum hydroxide was suspended (113 µg/mL) in buffer, and varying concentrations of each of compounds E, F, G, and H are added. The suspensions are allowed to equilibrate, and the concentration of each compound in solution at equilibrium is measured. The amount of compound adsorbed (weight/weight) is plotted against the concentration in solution to generate the adsorption isotherm. Adsorption capacity and adsorptive coefficient are calculated for each compound by double reciprocal analysis; the results are summarized in the following table. The data show significant binding of phosphorus containing groups described herein.

| Compound | Adsorptive Capacity (mg Compound/mg Al) | Adsorption Coefficient (mL/mg) |
|---|---|---|
| E | 1.02 | 42 |
| F | 0.70 | 106 |
| G | 0.59 | 90 |
| H | 0.73 | 165 |

Method Example

Compound B is coupled to Rat IgG (approximately 148 kDa MW) under conditions of moderate loading (approximately 20 equivalents compound B) and high loading (approximately 200 equivalents compound B). The linker loading of the product conjugates is analyzed by mass spectrometry. Treatment with 20 equivalents introduced a mean of approximately 10 linkers per IgG molecule, and treatment with 200 equivalents introduced a mean of approximately 45 linkers per IgG molecule. It is to be understood that the isolated compound B-Rat IgG conjugates may contain varying amounts of loading around the mean value. It is to be further understood that the mean value generally corresponds with the majority product.

Each conjugate product (0.6 mg/mL) is equilibrated with Rehydragel HPA aluminum hydroxide adjuvant (1.2 mg/mL), and the mixtures are diluted 1:3 in human serum and evaluated for retention of Rat IgG to adjuvant in a serum elution assay. The results are summarized in the following table:

TABLE

Elution of Linker-modified IgG from Aluminum Hydroxide Adjuvant in Human Serum

| Elution Time, hr | Unmodified IgG IgG Released | | IgG with 10 conjugates (P10) IgG Released | | IgG with 45 conjugates (P45) IgG Released | |
|---|---|---|---|---|---|---|
| | ng/ml | % | ng/ml | % | ng/ml | % |
| 0 | 1425 | 1 | 213 | 0 | 1 | 0.00 |
| 1 | 130291 | 104 | 37685 | 30 | 50 | 0.04 |
| 4 | 109229 | 87 | 55624 | 45 | 74 | 0.06 |
| 24 | 143918 | 115 | 75855 | 61 | 79 | 0.06 |

Method Example

Compound B-Rat IgG conjugates with various degrees of loading are prepared. The Rat-IgG is coupled with compound B as described herein. Briefly, reaction of the Rat-IgG and compound B at different molar ratios affords protein products with different conjugation loading. It is to be understood herein that although the resulting loading is related to the amount of conjugating agent used, depending upon the conjugating agent and upon the antigen, there may not be a linear relationship between the resulting loading and the amount of conjugating agent used. The degree of conjugation or loading is determined by mass spectrometry, which is applicable for a wide range of molecular weights, from for example, one kDa to several hundred kDa. Mass spectral analysis of unmodified Rat IgG (native) and the various conjugated Rat IgG shows the following loadings:

Compound B-DEC-205 Antibody Conjugates

| Example | Phosphonate Loading (No. determined by MS) | Phosphonylating Reagent (equivalents) |
|---|---|---|
| compound B-DEC-205 antibody-P5 | 5 | 15 |
| compound B-DEC-205 antibody-P10 | 10 | 40 |
| compound B-DEC-205 antibody-P17 | 17 | 72 |
| compound B-DEC-205 antibody-P23 | 23 | 49 |
| compound B-DEC-205 antibody-P30 | 30 | 150 |
| compound B-DEC-205 antibody-P36 | 36 | 125 |
| compound B-DEC-205 antibody-P45 | 45 | 292 |

The various degrees of loading are used to determine how many conjugate molecules are required to prepare an irreversible or substantially irreversible protein AH complex. The conjugated IgGs are combined with AH, and the extent of elution of protein from the AH particles in human serum is measured. The results shown in FIG. 1 indicate that time-dependent elution of protein occurs for the preparations containing 5-17 linkers. For protein modified with >17 linkers, the protein is irreversibly or substantially irreversibly bound to the aluminum hydroxide particles.

TABLE

Elution of Linker-modified IgG from Aluminum Hydroxide Adjuvant in Human Serum showing percentage elution of IgG

| | Elution Time (hr) | | | |
|---|---|---|---|---|
| | 0 | 1 | 4 | 24 |
| Rat IgG | 0.8 ± 0.1 | 93.5 ± 2.5 | 98.6 ± 1.8 | 100.3 ± 5.6 |
| P5 conjugate | 0.1 ± 0.0 | 26.2 ± 2.8 | 37.1 ± 2.3 | 55.8 ± 2.2 |
| P10 conjugate | 0.1 ± 0.1 | 23.6 ± 1.3 | 33.1 ± 2.9 | 45.8 ± 3.1 |
| P17 conjugate | 0 | 2.3 ± 0.2 | 3.1 ± 2.5 | 10 ± 1.4 |
| P23 conjugate | 0 | 0.2 ± 0.1 | 0.3 ± 0.1 | 0.3 ± 0.1 |
| P30 conjugate | 0 | 0.1 ± 0.0 | 0.1 ± 0.1 | 0.0 ± 0.1 |
| P36 conjugate | 0 | 0.0 ± 0.1 | 0.0 ± 0.1 | 0.1 ± 0.1 |
| P45 conjugate | 0 | 0 | 0.1 ± 0.1 | 0.1 ± 0.0 |

Method Example

Compound B-DEC-205 antibody conjugates with various degrees of loading are prepared. NLDC-145 is a hybridoma from which an antibody to DEC-205 is prepared. DEC-205 (or CD205) is a cell surface protein expressed on dendritic cells in animals, such as mice and humans. A rat monoclonal antibody against mouse DEC-205 is prepared according to conventional methods. The DEC-205 antibody is coupled with compound B as described herein. Briefly, reaction of the antibody with compound B at different molar ratios affords protein products with different conjugation loading. It is to be understood herein that although the resulting loading is related to the amount of conjugating agent used, depending upon the conjugating agent and upon the antigen, there may not be a linear relationship between the resulting loading and the amount of conjugating agent used. The degree of conjugation or loading is determined by mass spectrometry, which is applicable for a wide range of molecular weights, from for example, one kDa to several hundred kDa. Mass spectral analysis of unmodified DEC205 (native) and the various conjugated DEC205 shows the degree of loading.

Method Example

Lysozymes are proteins reported to be negligibly complexed by aluminum hydroxide (Hem, et. al., *Vaccine* 1995, 13, 41-44). Compound B is coupled to egg white lysozyme. Mass spectral analysis of the conjugation product indicates a mixture of unreacted lysozyme, mono-phosphonylated lysozyme, and bis-phosphonylated lysozyme, with the major component being the mono-phosphonylated lysozyme (compound H) and the minor component being the bis-phosphonate. Without further purification, compound H in varying concentrations is equilibrated with Rehydragel HPA aluminum hydroxide (20-26 µg/mL) at 4° C. After centrifugation, the protein concentration in the supernatant is measured by a standard micro bicinchoninic acid protein assay procedure. Adsorption isotherms are generated by plotting phosphonylated protein adsorbed (weight/weight aluminum) against the concentration of free compound H in solution. The ratio of Free/Bound H is plotted against concentration, and the adsorptive capacity and adsorption coefficient are obtained from the slope and intercept of a standard regression line. The results show a linear relationship between the free H and bound H, and the concentration of H. The linear dose response indicates that phosphonylated lysozyme H transforms lysozyme from a protein that shows poor electrostatic binding with aluminum hydroxide to a protein that shows increased affinity for aluminum hydroxide.

Method Example

Compound B-Lysozyme-P2 is prepared in a similar manner using a greater excess of conjugating agent compound B. To determine the magnitude of immunogenic enhancement for the linker-modified protein, a dose response is evaluated comparing a range of doses of compound B-Lysozyme-P2 and AH, to a range of doses of unmodified hen egg lysozyme and AH, according to the following table:

| Group | AH | Lysozyme Dose | Linker | # of mice |
|---|---|---|---|---|
| 1 | 1.2 mg/mL | — | − | 4 |
| 2 | 1.2 mg/mL | 10 µg | − | 8 |
| 3 | 1.2 mg/mL | 10 µg | + | 8 |
| 4 | 1.2 mg/mL | 3 µg | − | 8 |
| 5 | 1.2 mg/mL | 3 µg | + | 8 |
| 6 | 1.2 mg/mL | 1 µg | − | 8 |
| 7 | 1.2 mg/mL | 1 µg | + | 8 |
| 8 | 1.2 mg/mL | 0.3 µg | − | 8 |
| 9 | 1.2 mg/mL | 0.3 µg | + | 8 |

| Group | AH | Lysozyme Dose | Linker | # of mice |
|---|---|---|---|---|
| 10 | 1.2 mg/mL | 0.1 µg | – | 8 |
| 11 | 1.2 mg/mL | 0.1 µg | + | 8 |

Mice are injected on day 0 and day 21. Blood is collected on day 21 and on day 35. Serum anti-lysozyme IgG and anti-lysozyme IgG subclasses are measured by ELISA assay.

Method Example

Figure 2:
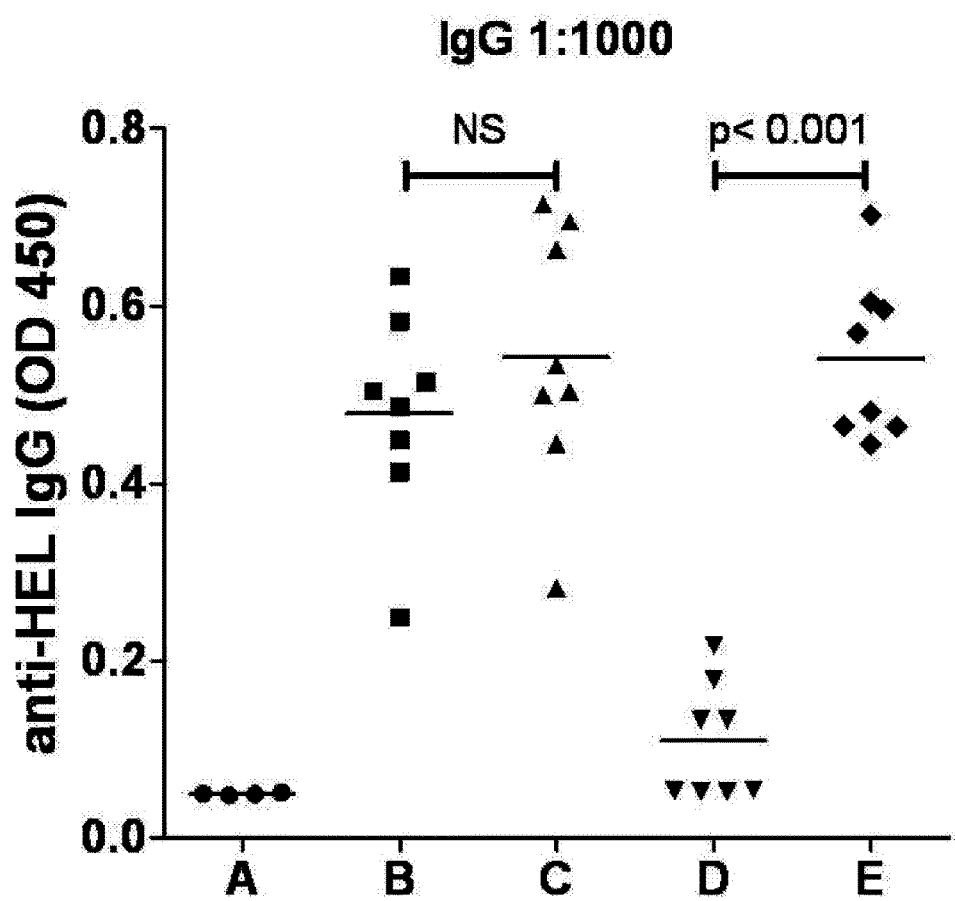
FIG. 2 shows a dose response comparison of conjugated and unconjugated lysozyme for immunological response.

Dose response comparison of conjugated and unconjugated lysozyme immunological response. Three preparations are investigated: (A), lysozyme alone (10 µg dose); (B), lysozyme (10 µg dose)+AH; (C), lysozyme-P2 (2 conjugate load, 10 µg dose)+AH; (D) lysozyme (1 µg dose)+AH; (E), lysozyme-P2 (1 µg dose)+AH. Mice groups are treated with A, B, C, D, and E. The anti-lysozyme antibody production in each experiment is shown in FIG. 2. Lysozyme (16 kDa MW) alone (A) does not show a significant induction of antibody response as expected. At a 10 µg dose, both unmodified (B) lysozyme+AH and conjugated-lysozyme (C) gave maximal responses; the unmodified lysozyme response is consistent with previous reports. At a 1 µg dose, the unmodified lysozyme (D) does not show a significant induction of antibody response; however, the conjugated-lysozyme (E) shows a maximal response at the 1 µg dose and statistically identical to that observed with the 10 µg dose. The data support the conclusion that conjugated antigens described herein are capable of providing at least a 10-fold increase in effective antigen concentration for proteins that lack intrinsic affinity for aluminum hydroxide.

Method Example

Figure 3:
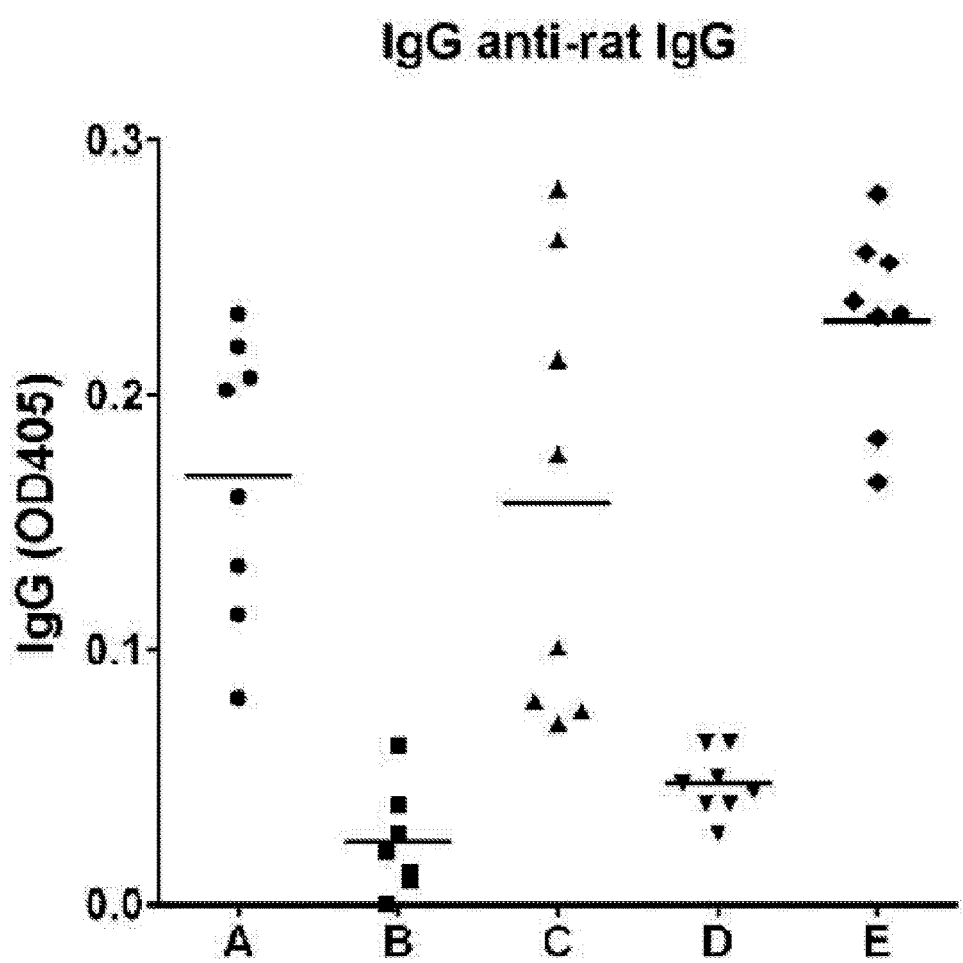
FIG. 3 shows a comparison of conjugated and unconjugated IgG for immunological response.

Comparison of conjugated and unconjugated IgG immunological response. Five preparations are investigated: (A), Compound B-DEC-205-P25 antibody conjugate prepared from NLDC-145+AH; (B) compound B-ovalbumin (OVA-P2)+AH; (C), Compound B-DEC-205-P25 antibody conjugate+OVA-P2+AH; (D) unconjugated DEC-205 antibody+OVA-P2+AH; (E), Compound B-Rat IgG-P17 conjugate prepared from commercially available rat serum (Jackson Immunoresearch Laboratories, West Grove, Pa.)+OVA-P2+AH. Mice groups are treated with A, B, C, D, and E at 50 µg doses of protein or protein conjugate. The IgG production in each experiment is shown in FIG. 3. Conjugated antigen compositions A, C, and E show significant IgG production, whereas unconjugated antigen composition D does not show significant IgG production. Antigen composition B (negative control) does not include any IgG, and therefore, does not show significant IgG production The data support the conclusion that conjugated antigens described herein are capable of providing a significant increase in effective antigen concentration.

Method Example

Conjugated diphtheria toxins. Commercially available mutant forms of diphtheria toxin, such as crm197, induce protection against diphtheria and are also used as carrier proteins in certain polysaccharide vaccines. Modified crm197 conjugated with the conjugating agents described herein, such as but not limited to, agents A, B, C, and D are prepared. Vaccine compositions are prepared including AH, and antibody responses, including IgG antibodies against crm197 and IgG antibody subclasses, in serum samples are determined using an ELISA assay. The antibody response is measured as a dose response, such as at doses of 1 µg and 0.3 µg, and comparing conjugated crm197 to unmodified crm197. Illustratively, the following protocol is followed:

| Group | AH | Crm197 Dose | Linker | # of mice |
|---|---|---|---|---|
| 1 | 1.2 mg/mL | — | – | 4 |
| 2 | 1.2 mg/mL | 1 µg | – | 8 |
| 3 | 1.2 mg/mL | 1 µg | + | 8 |
| 4 | 1.2 mg/mL | 0.3 µg | – | 8 |
| 5 | 1.2 mg/mL | 0.3 µg | + | 8 |

COMPOUND EXAMPLES

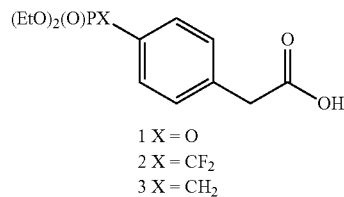

1 X = O
2 X = CF$_2$
3 X = CH$_2$

Example. Compound 1

Methyl 4-hydroxyphenylacetate (1.82 g, 11.95 mmol) in DCM (125 mL) was treated with diethylchlorophosphonate (1.9 mL, 13.15 mmol, 1.1 equiv) followed by TEA (2.0 mL, 14.3 mmol, 1.2 equiv). After stirring at rt under argon for 20 h the reaction mixture was washed with saturated NH$_4$Cl solution (50 mL), dried over Na$_2$SO$_4$ and concentrated to an amber oil. This oil was taken up in H$_2$O/THF (30 mL/80 mL) and was cooled to 4° C. LiOH solution (0.3M, 1.5 equiv) was added dropwise. TLC (25% EtOAc/hexanes/1% formic acid) showed no starting material after 30 min. The reaction mixture was quenched with 1N HCl and THF was removed by rotary evaporation. The remaining solution was made basic with saturated NaHCO$_3$ solution and was extracted with Et$_2$O (3×25 mL). The aqueous phase was acidified to pH 2 with 1 N HCl and was extracted with EtOAc (4×30 mL). The combined extracts were washed with brine, dried over Na$_2$SO$_4$ and concentrated to provide the crude product as a brown oil. Purification by column chromatography using 50% EtOAc/hexanes as eluent provided the carboxylic acid 1 as a clear oil (1.94 g, 56%). $^1$H NMR (CDCl$_3$): δ 10.23 (bs, 1H); 7.23 (d, 2H); 7.14 (d, 2H); 4.21 (m, 4H); 3.58 (s, 2H); 1.33 (t, 6H). $^{31}$P NMR (CDCl$_3$): δ −31.72 (s). HRMS (C$_{12}$H$_{17}$O$_6$P) calcd 311.0660 (M+Na)$^+$, found 311.0662.

Example. Compound 2

Methyl-4-[Diethyl phosphono(difluoromethylene)phenylacetate (Boutselis, et al, *J. Med. Chem.*, 2007, 50, 856-864) (0.91 g, 2.71 mmol) in 28 mL THF/H$_2$O (3/1) was stirred at 4° C. and 0.3M LiOH solution (13.5 mL, 4.1 mmol, 1.5 equiv) was added dropwise. After 45 min, TLC (30%

EtOAc/hexanes, Hanessian's stain) showed only a trace of starting material remaining. The reaction was quenched with 10% citric acid (50 mL) and THF was removed by rotary evaporation. The remaining aqueous solution was extracted with EtOAc (4×50 mL). The combined extracts were washed with brine, dried over $Na_2SO_4$, and concentrated to a pale yellow oil. Spectral data were consistent with published values (Zhang, et al, *Biochemistry*, 2003, 42, 12792-12804). The product was used without further purification (0.78 g, 89%).

Example. Compound 3

Compound 3 was synthesized according to the published procedure (Zhang, et al, *J. Label. Compd. Radiopharm.*, 2006, 49, 237-244).

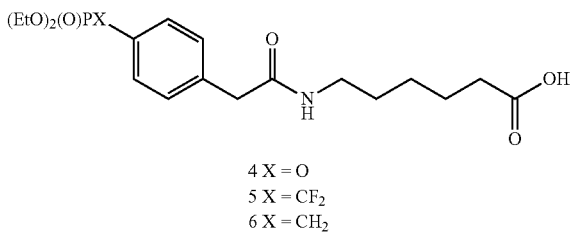

4 X = O
5 X = $CF_2$
6 X = $CH_2$

Example. Compounds 4-6

The following procedure for the synthesis of 5 is representative for compounds 4-6. Compound 2 (0.40 g, 1.24 mmol) in dry THF (14 mL) was treated with N-hydroxysuccinimide (0.14 g, 1.24 mmol, 1 equiv) and cooled in an ice bath. Diisopropylcarbodiimide (0.23 mL, 1.49 mmol, 1.2 equiv) was added. After stirring for 1.5 h, 6-aminocaproic acid (0.24 g, 1.83 mmol, 1.5 equiv) was added followed by DIEA (0.48 mL. 1.83 mmol, 1.5 equiv). The reaction came gradually to ambient temperature and was stirred under argon for 18 h. THF was removed by rotary evaporation and the residue was taken up in DCM (15 mL), washed with 10 mL 1N HCl, dried over $Na_2SO_4$ and concentrated to a yellow oil. Purification by column chromatography (20% EtOAc/hexanes to remove urea byproducts followed by 60% EtOAc/hexanes with 1% formic acid) provided the desired amide as a clear oil (0.47 g, 87%). Compound 4: $^1$H NMR ($CDCl_3$): δ 9.74 (bs, 1H); 7.19 (dd, 4H); 5.84 (bt, 1H); 4.23 (m, 4H); 3.53 (s, 2H); 3.22 (dd, 2H); 2.24 (t, 2H); 1.48 (m, 4H); 1.36 (t, 6H); 1.22 (m, 2H). $^{31}$P NMR ($CDCl_3$): δ −31.83 (s). HRMS ($C_{18}H_{28}NO_7P$) calcd 424.1501 (M+Na)$^+$, found 424.1499. Compound 5: $^1$H NMR ($CDCl_3$): δ 7.99 (bs, 3H); 7.46 (d, 2H); 7.29 (d, 2H); 6.75 (t, 1H); 4.12 (m, 4H); 3.50 (s, 2H); 3.11 (m, 2H); 2.20 (t, 2H); 1.44 (m, 6H); 1.21 (t, 6H). $^{31}$P NMR ($CDCl_3$): δ −19.37 (t). HRMS ($C_{19}H_{28}F_2NO_6P$) calcd 458.1520 (M+Na)$^+$, found 458.1518. Compound 6: $^1$H NMR ($CDCl_3$): δ 7.23 (m, 4H); 5.67 (bs, 1H); 4.06 (m. 4H); 3.55 (s, 2H); 3.27 (m, 2H); 3.25 (d, 2H); 2.23 (t, 2H); 1.47 (m, 4H); 1.27 (t, 6H); 1.19 (m, 2H). $^{31}$P NMR ($CDCl_3$): δ 1.58 (s). HRMS ($C_{19}H_{30}NO_6P$) calcd 400.1889 (M+H)$^+$, found 400.1893.

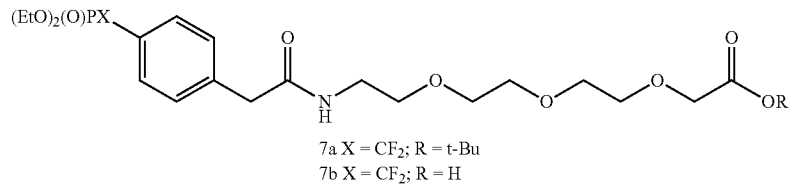

7a X = $CF_2$; R = t-Bu
7b X = $CF_2$; R = H

Example. Compound 7a

Compound 2 (0.13 g, 0.41 mmol) in dry THF (4 mL) was treated with N-hydroxysuccinimide (0.05 g, 0.41 mmol, 1 equiv) and cooled in an ice bath. DICD (0.08 mL, 0.49 mmol, 1.2 equiv) was added. After 1.5 h, amine 9 (0.13 g, 0.49 mmol, 1.2 equiv) was added followed by $NEt_3$ (0.07 mL, 0.49 mmol, 1.2 equiv). The reaction came gradually to rt while stirring under argon. THF was removed by rotary evaporation and the residue was taken up in DCM (10 mL), washed with 1N HCl, dried over $Na_2SO_4$ and concentrated. Purification by column chromatography (10% $Et_2O$/DCM to remove urea byproducts, 50% $Et_2O$/DCM/1% formic acid) provided the desired amide as an oil (0.15 g, 64%). $^1$H NMR ($CDCl_3$): δ 7.53 (d, 2H); 7.36 (d, 2H); 6.31 (s, 1H); 4.15 (m. 4H); 3.97 (s, 2H); 3.73 (m, 10H); 3.55 (s, 2H); 3.44 (m, 2H); 1.43 (s, 9H); 1.28 (t, 6H). $^{31}$P NMR ($CDCl_3$): δ −19.20 (t). HRMS ($C_{25}H_{40}F_2NO_9P$) calcd 568.2487 (M+H)$^+$, found 568.2492.

Example. Compound 7b

Ester 7a (0.86 g, 1.51 mmol) was treated with 8 mL TFA/DCM/$^i$Pr$_3$SiH (3/3/1). After stirring at rt for 3 h, TLC (4% MeOH/DCM, 1% formic acid, Hanessian's stain) showed no starting material remaining. Solvent was removed by rotary evaporation and the residue was co-evaporated with cyclohexane (5×2 mL) to provide the product as a pale orange oil, which was used without further purification (0.75 g, 97%). $^1$H NMR ($CDCl_3$): δ 7.46 (d, 2H); 7.34 (d, 2H); 6.50 (s, 1H); 4.17 (m, 4H); 4.10 (s, 2H); 3.63-3.36 (m, 14H); 1.28 (t, 6H). $^{31}$P NMR ($CDCl_3$): δ −19.18 (t). HRMS ($C_{21}H_{32}F_2NO_9P$) calcd 534.1681 (M+Na)$^+$, found 534.1686.

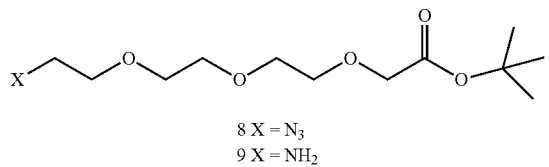

8 X = $N_3$
9 X = $NH_2$

Example. Compound 8

NaH, 60% dispersion (1.80 g, 45.0 mmol, 1.9 equiv) was washed with hexanes (3×50 mL). The washed sodium hydride was suspended in THF (90 mL) and azidotriethylene glycol, (Jeong and O'Brien, *J. Org. Chem.*, 2001, 66, 4799-4802) (4.11 g, 23.5 mmol) was added dropwise followed by dropwise addition and tert-butyl bromoacetate (4.40 mL, 29.8 mmol, 1.3 equiv). The mixture was stirred under argon for 18 h. The reaction was quenched with saturated NH$_4$Cl solution and THF was removed by rotary evaporation. The remaining aqueous mixture was extracted with Et$_2$O (4×75 mL). The combined extracts were washed with brine, dried over Na$_2$SO$_4$, and concentrated to give an orange-red oil. Purification by column chromatography (15% EtOAc/hexanes, 30% EtOAc/hexanes) provided the product as a pale orange oil (2.71 g, 40%). $^1$H NMR (CDCl$_3$): δ 4.02 (s, 2H); 3.70-3.65 (m, 10H); 3.39 (t, 2H); 1.47 (s, 9H). HRMS (C$_{12}$H$_{23}$N$_3$O$_5$) calcd 312.1535 (M+Na)$^+$, found 312.1539.

Example. Compound 9

Compound 8 (2.71 g, 9.36 mmol) in dry CH$_3$CN (80 mL) was treated with Ph$_3$P (2.85 g, 9.80 mmol, 1.05 equiv). After stirring at rt under argon for 4 h, water (100 mL) was added and the reaction was stirred overnight. Organic solvent was removed by rotary evaporation and the remaining aqueous mixture was chilled to 0° C. The white solid that formed was removed by filtration and the filtrate was extracted with DCM (10×30 mL). The combined extracts were washed with brine, dried over Na$_2$SO$_4$ and concentrated to an orange oil. Purification by column chromatography (100% EtOAc, 25% MeOH/EtOAc) provided the product as an orange oil (1.14 g, 46%). $^1$H NMR (CDCl$_3$): δ 4.01 (s, 2H); 3.71-3.60 (m, 8H); 3.50 (t, 2H); 2.86 (bs, 2H) 1.46 (s, 9H). HRMS (C$_{12}$H$_{25}$NO$_5$) calcd 263.1733 (M), found 263.1737.

remove the bulk of the urea by-product. The filtrate was concentrated to provide an oil. Purification by column chromatography (15% Et$_2$O/DCM, 2% MeOH/DCM/1% formic acid) provided the product (0.09 g, 57%). Compound 10: $^1$H NMR (CDCl$_3$): δ 7.17 (d, 2H); 7.08 (d, 2H); 6.14 (s, 1H); 4.14 (m. 4H); 3.42 (s, 2H); 3.13 (m, 2H); 2.75 (s, 4H); 2.51 (t, 2H); 1.61 (m, 2H); 1.41 (m, 4H); 1.28 (t, 6H). $^{31}$P NMR (CDCl$_3$): δ −31.47 (s). HRMS (C$_{22}$H$_{31}$N$_2$O$_9$P) calcd 521.1665 (M+Na)$^+$, found 521.1671. Compound 11: $^1$H NMR (CDCl$_3$): δ 7.52 (d, 2H); 7.33 (d, 2H); 6.08 (bs, 1H); 4.15 (m. 4H); 3.52 (s, 2H); 3.18 (m, 2H); 2.78 (s, 4H); 2.55 (t, 2H); 1.69 (m, 2H); 1.48 (m, 4H); 1.41 (t, 6H). $^{31}$P NMR (CDCl$_3$): δ −18.99 (t). HRMS (C$_{23}$H$_{31}$F$_2$N$_2$O$_8$P) calcd 533.1864 (M+H)$^+$, found 533.1872. Compound 12: $^1$H NMR (CDCl$_3$): δ 7.21 (m, 4H); 5.81 (bs, 1H); 3.99 (m. 4H); 3.49 (s, 2H); 3.19 (m, 2H); 3.10 (d, 2H); 2.80 (s, 4H); 2.55 (t, 2H); 1.69 (m, 2H); 1.39 (m, 4H); 1.22 (t, 6H). $^{31}$P NMR (CDCl$_3$): δ 1.14 (s). HRMS (C$_{23}$H$_{33}$N$_2$O$_8$P) calcd 519.1872 (M+Na)$^+$, found 519.1881.

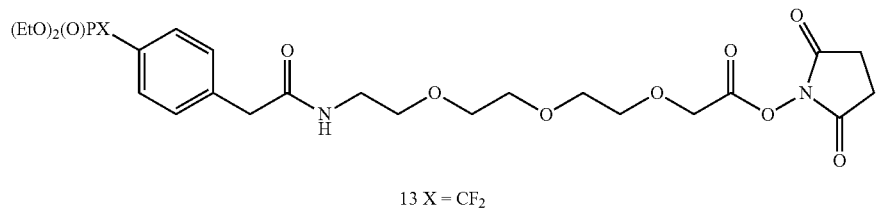

13 X = CF$_2$

Example. Compound 13

Carboxylic acid 7b (0.34 g, 0.66 mmol) and N-hydroxysuccinimide (0.08 g, 0.70 mmol, 1.1 equiv) in THF (2 mL) was cooled to 4° C. and then treated with DICD (0.12 mL, 0.77 mmol, 1.2 equiv). The reaction stirred under argon for 8 h. The reaction mixture was then cooled to −78° C. and filtered through a plug of glass wool to give the product as a clear oil with some remaining diisopropyl urea. Attempts to purify the product by column chromatography resulted in decomposition, thus it was used without further purification (0.51 g).

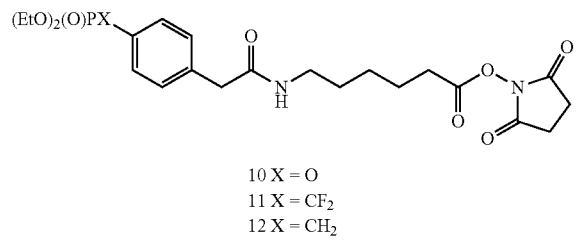

10 X = O
11 X = CF$_2$
12 X = CH$_2$

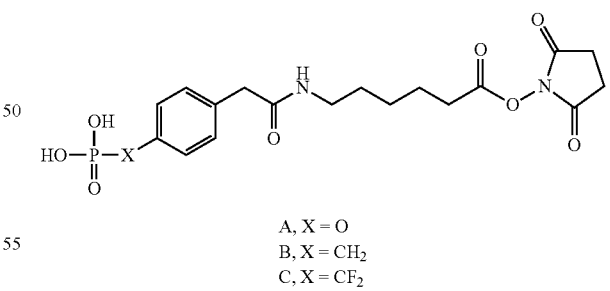

A, X = O
B, X = CH$_2$
C, X = CF$_2$

Example. Compounds 10-12

Synthesis of 11 is representative of the procedure used for the synthesis of N-hydroxysuccinimidyl esters 10-12. Carboxylic acid 5 (0.13 g, 0.30 mmol) in dry THF (4 mL) was treated with N-hydroxysuccinimide (0.034 g, 0.30 mmol, 1 equiv) and was cooled in an ice bath. DICD (0.05 mL, 0.32 mmol, 1.1 equiv) was added. The reaction stirred at 4° C. for 20 h under argon. The reaction mixture was cooled to −78° C. and was filtered through a plug of glass wool to

Example. Compounds A-C

Synthesis of C is representative of the procedure used for the synthesis of phosphonic acids A-C. Compound 11 (0.10 g, 0.19 mmol) was dissolved in DCM (2 mL) and the mixture was stirred at −20° C. under argon. TMSI (0.08 mL, 0.56 mmol, 3 equiv) was added and the reaction mixture was stirred at −20° C. for 18 h. Solvent was removed by rotary evaporation and the dark residue was co-evaporated (3×2 mL) with acetone. The dark residue was washed with Et₂O (3×2 mL) and was triturated in THF. Gradually, a yellow precipitate formed that was collected by filtration and washed with Et₂O to provide the product (0.05 g, 52%). Compound A: ¹H NMR (DMSO-d₆): δ 7.99 (t, 1H); 7.18 (d, 2H); 7.05 (d, 2H); 3.33 (s, 2H); 3.01 (m, 2H); 2.79 (s, 4H); 2.63 (t, 2H); 1.60 (m, 2H); 1.36 (m, 4H). ³¹P NMR (DMSO-d₆): δ −30.63 (s). HRMS (C₁₈H₂₃N₂O₉P) calcd 443.1219 (M+H)⁺, found 443.1224. Compound B: ¹H NMR (DMSO-d₆): δ 7.99 (t, 1H); 7.13 (m, 4H); 3.31 (s, 2H); 2.99 (m, 2H); 2.89 (d, 2H); 2.79 (s, 4H); 2.63 (t, 2H); 1.58 (m, 2H); 1.37 (m, 4H). ³¹P NMR (DMSO-d₆): δ −3.38 (s). HRMS (C₁₉H₂₅N₂O₈P) calcd 463.1246 (M+Na)⁺, found 463.1248. Compound C: ¹H NMR (DMSO-d₆): δ 8.08 (t, 1H); 7.43 (d, 2H); 7.32 (d, 2H); 3.42 (s, 2H); 3.01 (m, 2H); 2.79 (s, 4H); 2.63 (t, 2H); 1.60 (m, 2H); 1.39 (m, 4H). ³¹P NMR (DMSO-d6): δ −21.53 (t). HRMS (C₁₉H₂₃F₂N₂O₈P) calcd 477.1238 (M+H)⁺, found 477.1232.

Example. Compound 14

4-Hydroxyphenylacetic acid (0.79 g, 5.19 mmol) in 50 mL dioxane was treated with N-hydroxysuccinimide (0.66 g, 5.7 mmol, 1.1 equiv). Diisopropylcarbodiimide (0.90 mL, 5.7 mmol, 1.1 equiv) was added and the reaction mixture stirred at room temperature for 18 h under a drying tube. The precipitate that formed was removed by filtration and the filtrate was treated with a solution of p-nitrobenzylamine hydrochloride (0.98 g, 5.19 mmol, 1.0 equiv) in 30 mL H₂O and 15 mL dioxane. The mixture was stirred at 50° C. for 4 h, cooled to rt and acidified to pH 1 with 1M HCl. Extraction with EtOAc (4×20 mL), followed by a brine wash of the combined extracts, drying over Na₂SO₄ and concentration gave 14 as a white solid that was used without further purification. (1.36 g, 92%).

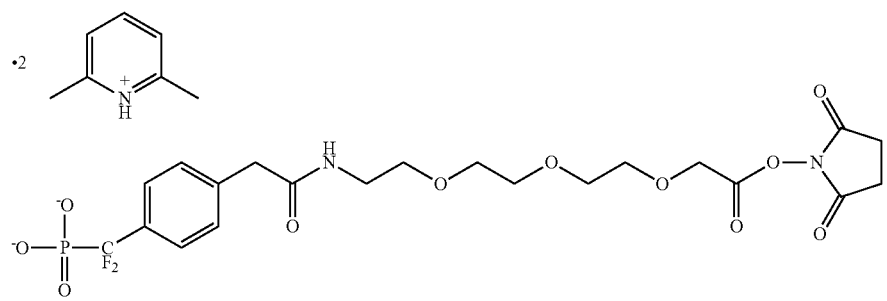

D

Example. Compound D

Compound 13 (0.15 g, 0.25 mmol) in DCM (3 mL) was cooled to −20° C., treated with 2,6-lutidine (0.06 mL, 0.52 mmol, 2.1 equiv) followed by TMSI (0.07 mL, 0.50 mmol, 2 equiv). The reaction was stirred under argon at −20° C. for 20 h. Solvent was removed by rotary evaporation and the dark residue was co-evaporated (3×2 mL) with acetone. The dark residue was washed with Et₂O (3×2 mL). Trituration with Et₂O, THF, EtOAc and DCM all failed to provide a solid. ¹H NMR of the crude oil indicates the presence of D along with minor impurities. ¹H NMR (CDCl₃): δ 8.12 (t, 2H); 7.45 (d, 6H); 7.20 (d, 2H); 6.97 (bs, 1H); 4.44 (s, 2H); 3.71-3.51 (m, 12H); 3.35 (m, 2H); 2.80 (s, 4H); 2.68 (s, 12H). ³¹P NMR (CDCl₃): δ −19.59 (t).

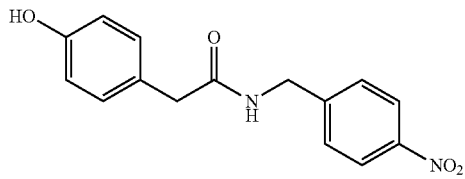

14

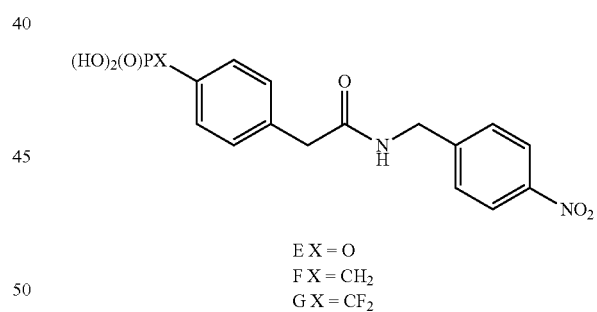

E X = O
F X = CH₂
G X = CF₂

Example. Compound E

Compound E was synthesized in two steps via compound 14. Compound 14 (0.29 g, 1.01 mmol) in 3 mL DCM was treated with POCl₃ (0.14 mL, 1.52 mmol, 1.5 equiv) and was cooled to 0° C. with stirring under argon. Solvent was removed after 1.5 h and the residue was taken up in 5 mL THF and saturated NaHCO₃ was added until the pH reached 7. The mixture was stirred for 1 h, the pH was then adjusted to 1 with 1M HCl, and the reaction mixture was extracted with EtOAc (4×10 mL). The combined extracts were washed with brine, dried over Na₂SO₄ and concentrated to a yellow solid used without further purification (0.13 g, 19%). ¹H NMR (DMSO-d₆): δ 8.70 (t, 1H); 8.16 (d, 2H);

7.46 (d, 2H); 7.22 (d, 2H); 7.07 (d, 2H); 4.37 (d, 2H); 3.46 (s, 2H). $^{31}$P NMR (DMSO-d$_6$): δ −30.61 (s). HRMS (C$_{15}$15$_3$N$_2$O$_7$P) calculated 367.0695 (M+H)$^+$, found 367.0700.

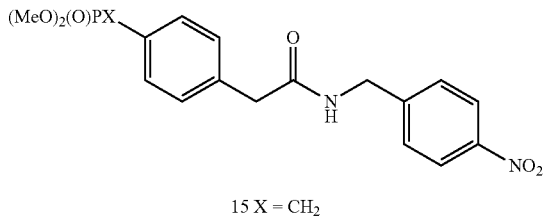

15 X = CH$_2$

Example. Compound 15

4-[(Dimethylphosphono)methyl]phenylacetic acid, (Taylor, et al., *Tetrahedron*, 1998, 54, 1691-1714), (0.37 g, 1.43 mmol, 1 equiv) in 10 mL dioxane was treated with N-hydroxysuccinimide (0.17 g, 1.50 mmol, 1.05 equiv) and diisopropylcarbodiimide (0.23 mL, 1.50 mmol, 1.05 equiv). After stirring at rt under a drying tube for 16 h, the precipitate formed was filtered and the filtrate was concentrated to give 0.60 g of product contaminated with diisopropyl urea. A portion of this crude product (0.30 g, 0.71 mmol) was dissolved in THF (4 mL) and treated with p-nitrobenzylamine hydrochloride (0.13 g, 0.71 mmol, 1 equiv) and NEt$_3$ (0.21 mL, 1.50 mmol, 2.1 equiv). The reaction was stirred at rt under a drying tube for 18 h, diluted with DCM (15 mL), and quenched with 1M HCl (10 mL). The organic phase was washed with 1M HCl, dried over Na$_2$SO$_4$, and concentrated to a yellow oil which was used without further purification (0.28 g, 87%).

Example. Compound F

Compound F was synthesized in two steps via compound 15. Compound 15 (0.19 g, 0.48 mmol, 1 equiv) in 3 mL DCM was treated with TMSBr (0.32 mL, 2.4 mmol, 5 equiv) and was capped and stirred for 18 h at rt. Solvent was removed and the residue was coevaporated with DCM (2×2 mL) and acetone (2×2 mL). Trituration with Et$_2$O provided a pale yellow solid that was filtered and dried (0.13 g, 74%). $^1$H NMR (DMSO-d$_6$): δ 8.69 (t, 1H); 8.16 (d, 2H); 7.46 (d, 2H); 7.16 (s, 4H); 4.36 (d, 2H); 3.45 (s, 2H); 2.91 (d, 2H). $^{31}$P NMR (DMSO-d$_6$): δ −3.41 (s). HRMS (C$_{16}$H$_{17}$N$_2$O$_6$P) calculated 365.0903 (M+H)$^+$, found 365.0910.

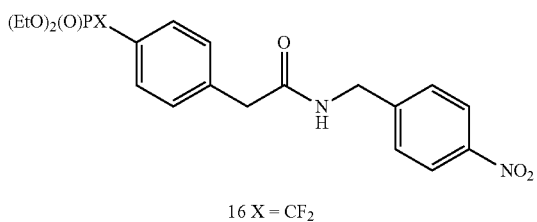

16 X = CF$_2$

Example. Compound 16

Compound 2 (0.46 g, 1.43 mmol, 1 equiv) in 10 mL dioxane was treated with N-hydroxysuccinimide (0.18 g, 1.6 mmol, 1.1 equiv) and diisopropylcarbodiimide (0.25 mL, 1.6 mmol, 1.1 equiv). After stirring at rt under a drying tube for 16 h, the precipitate formed was filtered and the filtrated was treated with p-nitrobenzylamine hydrochloride (0.27 g, 1.43 mmol, 1 equiv) and NaHCO$_3$ (0.13 g, 1.57 mmol, 1.1 equiv). The reaction was stirred at 50° C. for 18 h. The reaction was cooled to rt, acidified to pH 1 with 1M HCl and extracted with EtOAc (4×20 mL). The combined extracts were washed with brine, dried over Na$_2$SO$_4$ and concentrated to an orange syrup which was used without further purification. Crude yield: (0.56 g, 86%)

Example. Compound G

Compound G was synthesized in two steps via compound 16. Compound 16 (0.21 g, 0.46 mmol, 1 equiv) in 3 mL DCM was treated with TMSBr (0.30 mL, 2.3 mmol, 5 equiv) and was capped and stirred for 18 h at rt. Solvent was removed and the residue was coevaporated with DCM (2×2 mL) and acetone (2×2 mL). Trituration with Et$_2$O provided a pale yellow solid that was filtered and dried (0.14 g, 78%). $^1$H NMR (DMSO-d$_6$): δ 8.77 (t, 1H); 8.17 (d, 2H); 7.47 (m, 4H); 7.37 (m, 2H); 4.39 (d, 2H); 3.56 (s, 2H). $^{31}$P NMR (DMSO-d$_6$): δ −21.40 (t). HRMS (C$_{16}$H$_{15}$F$_2$N$_2$O$_6$P) calcd 401.0714 (M+H)$^+$, found 401.0717.

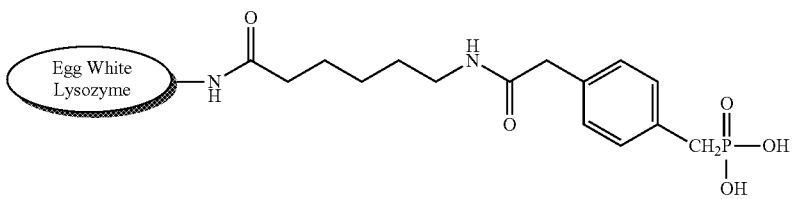

Example. Compound H

Solutions of egg white lysozyme, (10 mg/mL in phosphate-buffered saline, PBS) and Compound B (0.1M in DMSO) were prepared. Lysozyme solution (1 mL, 0.689 μmol) and B (27.6 μL, 2.76 μmol, 4 equiv) were combined in an Eppendorf tube and were tumbled at 0° C. for 18 h. The reaction mixture was applied to a Sephadex LH-20 column (15 cm×1 cm) and was eluted with H$_2$O. Fractions 2-4 were combined and lyophilized to yield 0.015 g of the conjugate as a white powder. Mass spectral analysis indicated that the product is a mixture of lysozyme and mono- and di-phosphonylated lysozyme, with mono-phosphonylated compound being the major component of the three and di-phosphonylated compound being the minor component.

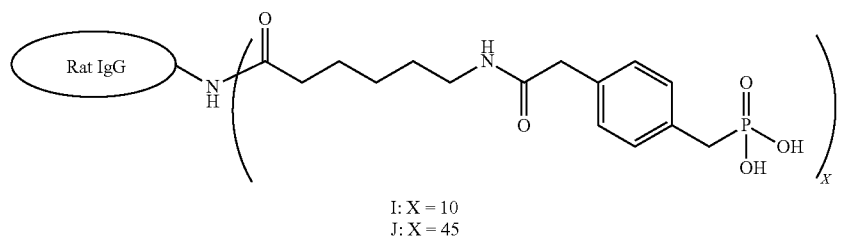

I: X = 10
J: X = 45

Example. Compound I

Rat IgG, 11.1 mg/mL in 0.01M sodium phosphate, 0.25M NaCl buffer at pH 7.6, was purchased from Jackson ImmunoResearch Laboratories, Inc. Rat IgG (0.35 mL 0.026 μmol) in an Eppendorf tube was treated with compound B (50 μL of a 7.5 mM solution in DMSO, 0.38 μmol, 15 equiv). The mixture was tumbled at 4° C. for 18 h. The reaction mixture was diluted with 0.6 mL water, transferred to a dialysis membrane (MWCO 6-8000) and was dialyzed against pure water at 4° C. over 12 h with 3 water changes. Lyophilization provided the product as a white solid (3.9 mg). Mass spectral analysis indicated the presence of approximately 10 phosphonate linkers per molecule.

Example. Compound J

Rat IgG (0.35 mL, 0.026 μmol) in an Eppendorf tube was treated with compound B (50 μL of a 0.15M solution in DMSO, 7.5 μmol, 288 equiv). The mixture was tumbled at 4° C. for 12 h. The reaction mixture was diluted with 0.6 mL water, transferred to a dialysis membrane (MWCO 6-8000) and was dialyzed against pure water at 4° C. over 12 h with 3 water changes. Lyophilization provided the product as a white solid (7.5 mg). Mass spectral analysis indicated the presence of approximately 45 phosphonate linkers per molecule.

Example. Adsorption Isotherm Procedures

Adsorption of Compound H (Egg white Lysozyme/Compound B conjugate) by Aluminum Hydroxide. Stock solutions of compound H and aluminum hydroxide were prepared. Compound H (2.52 mg) was dissolved in 10 mL MOPS (3-(N-morpholino)propanesulfonic acid) buffer, pH 7.4 to make a solution that was 252 μg/mL. This solution was further diluted, taking 1.40 mL and diluting to 4.00 mL, thus generating a stock solution of H that was 88.2 μg/mL. A 1 mg/mL solution of aluminum hydroxide (Rehydroagel HPA, 10.2 mg $Al^{3+}$/mL, Reheis, Berkeley Heights, N.J.) in MOPS buffer, pH 7.4 was prepared. Further dilution of this solution yielded a working solution with the concentration of 76 μg/mL. Twelve Eppendorf tubes were charged with aluminum hydroxide solution (0.45 mL, 34.2 μg). Varying volumes of compound H were added to 11 of the tubes, no lysozyme conjugate was added to the final tube. MOPS buffer was added so that the total volume of all tubes was 1.5 mL, generating 12 samples with a constant aluminum hydroxide concentration of 22.8 μg/mL and concentrations of compound H that varied from zero to 35.28 μg/mL. The tubes were tumbled for 1 h at 4° C. then centrifuged at 10,000 rpm for 7 min. The supernatant was analyzed in triplicate for compound H concentration by the micro bicinchoninic acid (BCA) assay. The amount of compound H adsorbed was determined by subtracting the amount remaining in the supernatant from the amount initially present. The adsorption isotherm for compound H by aluminum hydroxide was determined by plotting the concentration of H in solution against the amount of H adsorbed per μg of aluminum hydroxide.

Example. Adsorption of Compounds E, F, and G by Aluminum Hydroxide

The procedure described above for compound H was used with the following modifications. The constant aluminum hydroxide concentration in each trial was 113.33 μg/mL. Final concentrations of compounds being tested ranged from zero to 145 μg/mL. The samples were tumbled at rt. The concentration of compound in supernatant was determined by measuring the UV absorption of supernatant and calculating concentration by Beer's Law (the extinction coefficient was determined experimentally). Concentrations of compound adsorbed, adsorption isotherms and linear forms of adsorption isotherms were determined as described previously.

While certain embodiments of the present invention have been described and/or exemplified above, it is contemplated that considerable variation and modification thereof are possible. Accordingly, the present invention is not limited to the particular embodiments described and/or exemplified herein.

The following publications, and each additional publication cited herein, are incorporated herein by reference in their entirety.

1. Hem and HogenEsch, *Expert Review of Vaccines* 2007, 6, 685-698.
2. Hem, et al., *Vaccine* 1995, 13, 41-44.
3. Boutselis, et al., *J. Med. Chem.*, 2007, 50, 856-864.
4. Zhang, et al., *Biochemistry*, 2003, 42, 12792-12804.
5. Zhang, et al., *J. Label. Compd. Radiopharm.*, 2006, 49, 237-244.
6. Jeong and O'Brien, *J. Org. Chem.*, 2001, 66, 4799-4802.
7. Taylor, et al., *Tetrahedron*, 1998, 54, 1691-1714.

What is claimed is:

1. A conjugate comprising a protein or peptide covalently attached to an independently selected fragment of the formula (I)

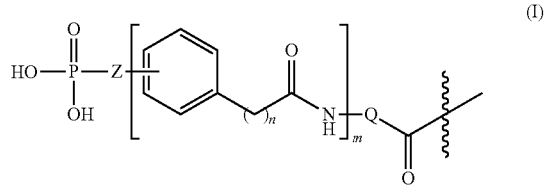

wherein
- Q is a polyvalent alkylene or heteroalkylene linker, each of which is optionally substituted;
- Z is O, —$CH_2$—, or $CF_2$—;
- m is an integer in the range from 1 to 3; and
- n is an integer in the range from 1 to 20;
- wherein the protein or peptide is directly attached to the carbonyl carbon of the Q-C=O group of the independently selected fragment of the formula (I), and wherein the protein or peptide is the terminal end of the conjugate.

2. The conjugate of claim 1 wherein the protein or peptide is an antigen.

3. The conjugate of claim 1 wherein m is 1 or 2.

4. The conjugate of claim 1 wherein n is 1 or 2.

5. The conjugate of claim 1 wherein Q is optionally substituted alkyleneamino(alkyl)$_2$, where each alkyl is independently selected.

6. The conjugate of claim 1 wherein Q is optionally substituted poly(oxyalkylene).

7. A method for vaccinating a patient or generating an immune response in a patient, the method comprising the step of administering to the patient a therapeutically effective amount of an immunogenic complex comprising the conjugate of claim 1 and an adjuvant.

8. The method of claim 7 wherein the adjuvant is an aluminum-containing adjuvant.

9. The conjugate of claim 1, wherein the protein or peptide comprises one or more lysines.

10. The conjugate of claim 1, wherein the conjugate is configured to function as an immunogenic compound and/or vaccine.

* * * * *